(12) United States Patent
Dardik et al.

(10) Patent No.: US 7,228,168 B2
(45) Date of Patent: Jun. 5, 2007

(54) SYSTEMS AND METHODS FOR ASSESSING AND MODIFYING AN INDIVIDUAL'S PHYSIOLOGICAL CONDITION

(75) Inventors: Irving I Dardik, Califon, NJ (US); Stanley S Reisman, Livingston, NJ (US)

(73) Assignee: Lifewaves International, Inc., Califon, NJ (US)

( * ) Notice: Subject to any disclaimer, the term of this patent is extended or adjusted under 35 U.S.C. 154(b) by 548 days.

(21) Appl. No.: 10/154,175

(22) Filed: May 21, 2002

(65) Prior Publication Data

US 2003/0013979 A1 Jan. 16, 2003

Related U.S. Application Data

(63) Continuation of application No. 09/609,087, filed on Jun. 30, 2000, now abandoned.

(51) Int. Cl.
*A61B 5/04* (2006.01)

(52) U.S. Cl. .................................. 600/520

(58) Field of Classification Search .......... 482/1–9, 482/900–902; 600/508–509, 519–520
See application file for complete search history.

(56) References Cited

U.S. PATENT DOCUMENTS

| | | | | |
|---|---|---|---|---|
| 3,518,985 A | 7/1970 | Quinton | ........................ | 128/2.06 |
| 3,675,640 A | 7/1972 | Gatts | ........................ | 272/2.05 R |
| 3,802,698 A | 4/1974 | Burian et al. | ............... | 272/57 R |
| 3,978,849 A | 9/1976 | Geneen | .................. | 128/2.05 T |
| 4,278,095 A | 7/1981 | Lapeyre | ..................... | 128/689 |
| 4,281,663 A | 8/1981 | Pringle | ....................... | 128/689 |
| 4,301,808 A | 11/1981 | Taus | ............................ | 128/687 |
| 4,358,105 A | 11/1982 | Sweeney, Jr. | ............... | 272/73 |
| 4,367,752 A | 1/1983 | Jimenez et al. | ............. | 128/689 |
| 4,408,613 A * | 10/1983 | Relyea | ........................ | 600/483 |
| 4,425,921 A | 1/1984 | Fujisaki et al. | ............. | 128/690 |
| 4,436,097 A | 3/1984 | Cunningham | ................ | 128/707 |
| 4,566,456 A | 1/1986 | Koning et al. | ........ | 128/419 PG |
| 4,566,461 A | 1/1986 | Lubell et al. | ................ | 600/481 |
| 4,613,129 A | 9/1986 | Schroeder et al. | ........... | 272/73 |
| 4,622,980 A | 11/1986 | Kunig | ......................... | 128/704 |

(Continued)

FOREIGN PATENT DOCUMENTS

CA 2091101 9/1993

(Continued)

OTHER PUBLICATIONS

Acker J.E., Jr. et al., "Assessing psychological problems from a cardiologist's point of view," (Abstract) *Advances in Cardiology*, 31 at 218-22 (1982).

(Continued)

*Primary Examiner*—Carl Layno
(74) *Attorney, Agent, or Firm*—Fish & Neave IP Group, Ropes & Gray LLP; Jeffrey C. Aldridge

(57) ABSTRACT

Systems and methods for assessing an individual's physiological condition are provided. Cycle and shape parameters are derived from a recorded time trace containing heart rate data collected while an individual performs a cyclic exercise routine. Individually tailored exercise regimens that are based on these parameters are generated and modified as desired.

9 Claims, 13 Drawing Sheets

U.S. PATENT DOCUMENTS

| | | | | |
|---|---|---|---|---|
| 4,683,891 | A | 8/1987 | Cornellier et al. | 128/630 |
| 4,719,920 | A | 1/1988 | Alt et al. | 128/419 PG |
| 4,788,983 | A | 12/1988 | Brink et al. | 128/734 |
| 4,807,639 | A | 2/1989 | Shimizu et al. | 128/690 |
| 4,867,442 | A | 9/1989 | Matthews | 272/93 |
| 4,883,063 | A | 11/1989 | Bernard et al. | 128/670 |
| 4,896,675 | A | 1/1990 | Ohsuga et al. | 128/671 |
| 4,938,228 | A | 7/1990 | Righter et al. | 128/690 |
| 5,001,632 | A * | 3/1991 | Hall-Tipping | 463/7 |
| 5,007,430 | A | 4/1991 | Dardik | 128/696 |
| 5,163,439 | A | 11/1992 | Dardik | 128/696 |
| 5,267,568 | A | 12/1993 | Takara | 128/687 |
| 5,410,472 | A * | 4/1995 | Anderson | 482/9 |
| 5,598,849 | A * | 2/1997 | Browne | 600/520 |
| 5,752,521 | A | 5/1998 | Dardik | 128/687 |
| 5,788,640 | A | 8/1998 | Peters | 600/483 |
| 5,810,737 | A | 9/1998 | Dardik | 600/500 |
| 5,921,891 | A * | 7/1999 | Browne | 482/8 |
| 5,941,837 | A | 8/1999 | Amano et al. | 600/595 |
| 5,999,854 | A | 12/1999 | Deno et al. | 607/17 |
| 6,261,103 | B1 | 7/2001 | Stephens et al. | 434/276 |
| 6,304,774 | B1 * | 10/2001 | Gorman | 600/520 |
| 6,361,503 | B1 | 3/2002 | Starobin et al. | 600/508 |
| 6,447,424 | B1 * | 9/2002 | Ashby et al. | 482/8 |
| 6,605,038 | B1 * | 8/2003 | Teller et al. | 600/300 |
| 6,662,032 | B1 | 12/2003 | Gavish et al. | 600/323 |
| 6,702,719 | B1 * | 3/2004 | Brown et al. | 482/8 |
| RE38,749 | E * | 6/2005 | Dardik | 600/500 |

FOREIGN PATENT DOCUMENTS

| | | |
|---|---|---|
| CN | 1095917 | 12/1994 |
| DE | 3045923 | 9/1981 |
| DE | 3409792 | 9/1984 |
| DE | 3532620 | 3/1986 |
| DE | 4338958 | 5/1994 |
| EP | 5949 | 12/1979 |
| EP | 117330 | 9/1984 |
| EP | 172747 | 2/1986 |
| EP | 181067 | 5/1986 |
| EP | 255621 | 2/1988 |
| EP | 419103 | 3/1991 |
| EP | 556702 | 8/1993 |
| EP | 922434 | 6/1999 |
| EP | 956819 | 11/1999 |
| FI | 8304152 | 5/1985 |
| FI | 8900776 | 8/1989 |
| FI | 9504300 | 3/1996 |
| FR | 2569158 | 2/1986 |
| FR | 2599616 | 12/1987 |
| GB | 2052051 | 1/1981 |
| GB | 2165352 | 4/1986 |
| GB | 2184361 | 6/1987 |
| GB | 2253706 | 9/1992 |
| GB | 2306659 | 5/1997 |
| JP | 07313474 | 12/1995 |
| WO | 85/00279 | 1/1985 |
| WO | 90/12538 | 11/1990 |
| WO | 93/14807 | 8/1993 |
| WO | 94/02904 | 2/1994 |
| WO | 97/22295 | 6/1997 |

OTHER PUBLICATIONS

Ades P.A. et al., "Hypertension, exercise and beta-adrenergic blockade," (Abstract) *Annals of Internal Medicine*, 109 (8) at 629-34 (Oct. 15, 1988).

Aizaki T. et al., "Development of an ambulatory 24-hour recording device of electrocardiogram and exercise intensity and its analytic system," (Abstract) *Japan Journal of Med. Electron. Biol. Eng.* 32/2 at 83-90 (1994).

Al-Aweel J.C. et al., "Postictal heart rate oscillations in partial epilepsy," *Neurology*, 53 at 1590-1592 (1999).

Balogun J.A. et al., "Cardiovascular adjustments and perceived exertion during exercise on the BAPS board," (Abstract) *Disability and Rehabilitation*, 17 (8) at 430-6 (Nov.-Dec. 1995).

Belardinelli R. et al., "Exercise training improves left ventricular diastolic filling in patients with dilated cardiomyopathy. Clinical and prognostic implications," (Abstract) *Circulation*, 91 (11) at 2775-84 (Jun. 1, 1995).

Brusis O.A., "Rehabilitating coronary patients through exercise," (Abstract) *Postgraduate Medicine*, 44 (1) at p. 131-5 (Jul. 1968).

Bryniarski L. et al., "Effect of exercise rehabilitation on heart rate variablility in hypertensives after myocardial infarction," (Abstract) *Journal of Hypertension*, 15 (12 pt 2) at 1739-43 (Dec. 1997).

Calzolari A.M. et al., "Rehabilitation of children after total correction of tetralogy of Fallot," (Abstract) *International Journal of Cardiology*, 28 (2) at 151-8 (Aug. 1990).

Cambach W. et al., "The effects of a community-based pulmonary rehabilitation programme on exercise tolerance and quality of life: a radomized controlled trial," (Abstract) *European Respiratory Journal*, 10 (1) at 104-13 (Jan. 1997).

Cerny F.J., "Relative effects of bronchial drainage and exercise for in-hospital care of patients with cystic fibrosis," (Abstract) *Phys. Ther.* 69/8 at 633-639 (1989).

Chen J. et al., "Ischemic tolerance the brain," *Neurology*, vol. 48, p. 306 (Feb. 1997).

Claus J. et al., "Special aspects of physical training during the rehabilitation stage of coronary patients," (Abstract) *Herz*, 16 (4) at 199-209 (Aug. 1991).

Cohen M. V. et al., "Ischaemic preconditioning: can the protection be bottled?," *The Lancet*, vol. 342 (Jul. 1993).

Cooney M.M. et al., "Hydraulic resistance exercise benefits cardiovascular fitness of spinal cord injured," (Abstract) Medicine and Science in Sports and Exercise, 18 (5) at 522-5 (Oct. 1986).

Crakes J.G. et al., "Endpoints of chronobiologic cardiovascular monitoring during pregnancy for planning exercise and assessing effects," (Abstract) *Progress in Clinical and Biological Research*, 341A at 605-14 Ref: 28 (1990).

Czernin J. et al., "Effect of short-term cardiovascular conditioning and low-fat diet on myocardial blood flow and flow reserve," (Abstract) *Circulation*, 92 (2) at 197-204 (Jul. 15, 1995).

Dardik Irving I., "The Great Law of the Universe," *Cycles* at 265-277 (Mar.-Apr. 1994).

Dardik Irving I., "The Law of Waves and the Invalidation of the Scientific Method," *Cycles*, vol. 45, No. 2 at 49-60 (Feb. 1995).

Dardik Irving I., "The Origin of Disease and Health, Heart Waves: The Single Solution to Heart Rate Variability and Ischemic Preconditioning," *Cycles*, vol. 46, No. 3 at 67-77 (Dec. 1996).

Dardik Irving I., "The Origin of Disease and Health, Heart Waves: The Single Solution to Heart Rate Variability and Ischemic Preconditioning," *Frontier Perspectives*, vol. 6, No. 2 at 18-32 (Spring/Summer, 1997).

Dardik Irving I., "Research proposals for studying mind-body interactions, Cardiocybernetics*: Relaxation through Exercise," *Advances, Journal of the Institute for the Advancement of Health*, vol. 8, No. 3 at 56-59 (Summer 1986).

De Vries H.A. et al., "Electromyographic comparison of single doses of exercise and meprobamate as to effects on muscular relaxation," (Abstract) *American Journal of Physical Medicine*, 51 (3) at 130-41 (Jun. 1972).

DiCarlo S. et al., "Hemodynamic and energy cost responses to changes in arm exercise technique," (Abstract) *Physical Therapy*, 63 (10) at 1585-92 (Oct. 1983).

Domenech R. J. et al. "Tachycardia preconditioning infarct size in dogs; Role of adenosine and protein Kinase C," (Oct. 1997).

Estok P.J. et al., "Jogging: cardiovascular benefits and risks," (Abstract) *Nurse Practitioner*, 11 (5) at 21-8 (May 1986).

Ewart C.K. et al. "Usefulness of self-efficacy in predicting overexertion during programmed exercise in coronary artery disease," (Abstract) *American Journal of Cardiology*, 57 (8) at 557-61 (Mar. 1, 1986).

Fletcher G.F., "Rehabilitative exercise for the cardiac patient. Early phase," (Abstract) *Cardiology Clinics*, 11 (2) at 267-75 Ref: 20 (May 1993).

Fletcher G.F. et al., "Continuous ambulatory electrocardiographic monitoring. Use in cardiac exercise programs," (Abstract) *Chest*, 71 (1) at 27-32 (Jan. 1977).

Folgering H. et al., "Exercise limitations in patients with pulmonary diseases," (Abstract) *International Journal of Sports Medicine*, 15 (3) at 107-11 (Apr. 1994).

Freedman R. et al., "Biofeedback and progressive relaxation treatment of sleep-onset insomnia: a controlled, all-night investigation," (Abstract) *Biofeedback and Self Regulation*, 1 (3) at 253-71 Journal code: A15 (Sep. 1976).

Fujita Y. et al., "Relationship between age-adjusted heart rate and anaerobic threshold in estimating exercise intensity in diabetics," (Abstract) *Diabetes Res. Clin. Pract.*, 8/1 at 69-74 (1990).

Fulcher K.Y. et al., "Randomised controlled trial of graded exercise in patients with the chronic fatigue syndrome," (Abstract) *BMJ (Clinical Research Ed.)*, 314 (7095) at 1647-52 (Jun. 7, 1997).

Garfinkel Alan et al., "Heart Rate Dynamics After Acute Cocaine Administration," *Journal of Cardiovascular Pharmacology*, vol. 19, No. 3 at 453-459 (1992).

Gho B. C. G. et al., "Myocardial Protection by Brief Ischemia in Noncardiac Tissue," *Circulation* vol. 94. No. 9 (Nov. 1996).

Goldberg A.P. et al., "Therapeutic benefits of exercise training for hemodialysis patients," (Abstract) *Kidney International Supplement*, 16 at S303-9 (Dec. 1983).

Gordon N.F. et al., "Exercise and mild essential hypertension," (Abstract) *Primary Care; Clinics in Office Practice*, 18 (3) at 683-94 Ref: 60 (Sep. 1991).

Greer M. et al., "Physiological responses to low-intensity cardiac rehabilitation exercises," (Abstract) *Physical Therapy*, 60 (9) at 1146-51 (Sep. 1980).

Hertzeanu H.L. et al., "Ventricular arrhythmias in rehabilitated and nonrehabilitated post-myocardial infarction patients with left ventricular dysfunction," (Abstract) *American Journal of Cardiology*, 71 (1) at 24-7 (Jan. 1, 1993).

Hooker S.P. et al., "Physiologic effects of electrical stimulation leg cycle exercise training in spinal cord injured persons," (Abstract) *Archives of Physical Medicine and Rehabilitation*, 73 (5) at 470-6 (May 1992).

Hrushesky William J. M., "Timing is everything," *The Sciences*, at 32-37 (Jul./Aug. 1994).

Iwadare M. et al., "Exercise prescription for physical training in hypertensive patients," (Abstract) *Nippon Rinsho. Japanese Journal of Clinical Medicine*, 50 Suppl. at 160-7 (May 1992).

Jovanovic-Peterson L. et al., "Randomized trial of diet versus diet plus cardiovascular conditioning on glucose levels in gestational diabetes," (Abstract) *American Journal of Obstetrics and Gynecology*, 161 (2) at 415-9 (Aug. 1989).

Kamata H. et al., "Semi-supervised exercise using a step machine at home after myocardial infarction," (Abstract) *Journal of Cardiology*, 29 (1) at 23-8 (Jan. 1997).

Katoh J. et al., "Cardiorespiratory effects of weight reduction by exercise in middle-aged women with obesity," (Abstract) *Journal of International Medical Research*, 22 (3) at 160-4 (May/Jun. 1994).

Kellermann J.J., "Rationale of exercise therapy in patients with angina pectoris with normal and impaired ventricular function," (Abstract) *Chest. 101/5 Suppl.* at 322S-325S (1992).

King C.N. et al., "Exercise testing and prescription. Practical recommendations for sedentary," (Abstract) *Sports Medicine*, 21 (5) at 326-36 (May 1996).

Koch S.M., "Effect of passive range of motion on intracranial pressure in neurosurgical patients," (Abstract) Journal of Critical Care, 11 (4) at 176-9 (Dec. 1996).

Kohno M. et al., "Effects of exercise therapy on blood pressure and hormonal factors in subjects with borderline and mild hypertension," (Abstract) *Bull. Phys. Fitness Res. Inst.* -/72 at 81-86 (1989).

Leitch J.W. et al., "Randomized trial of a hospital-based exercise training program after acute myocardial infarction: cardiac autonomic effects," (Abstract) *Journal of the American College of Cardiology*, 29 (6) at 1263-8 (May 1997).

Malik Marek et al., "Heart Rate Variability: Standards of Measurement, Physiological Interpretation, and Clinical Use," *A.N.E.*, vol. 1, Pt. 1, at 151-181 (Apr. 1996).

Malikov V.A. et al., "Selection of optimal training exercise and training schedule for patients with ischemic heart disease at the early periods after aortocoronary bypass," (Abstract) *Kardiologiia* 31 (7) at 17-20 (Jul. 1991).

Malpas et al., "Circadian Variation Of Heart Rate Variability," Cardiovascular Research, vol. 24, at 210-213 (1990).

Marcelino J. et al., "Assessment of a circuit of exercises through heart rate response," (Abstract) *International Journal of Cardiology*, 49 (2) at 153-8 (Apr. 1995).

Masuoka, Toshiharu, "A Clinical Study of Exercise Training after Reperfusion Therapy in Patients with Myocardial Infarction," (Abstract) *Abstracts For Hiroshima Daigaku Igaku Zasshi*, 43(3) at 149-160 (1995).

Maynard T., "Exercise: Part II. Translating the exercise prescription," (Abstract) *Diabetes Educator* 17 (5) at 384-95 Ref: 13 (Sep.-Oct. 1991).

Mead W.F., "Exercise rehabilitation after myocardial infarction," (Abstract) *American Family Physician*, 15 (3) at 121-5 (Mar. 1977).

Melton-Rogers S et al., "Cardiorespiratory responses of patients with rheumatoid arthritis during bicycle riding and running in water," (Abstract) *Physical Therapy*, 76 (10) at 1058-65 (Oct. 1996).

Mertens D.J. et al., "Exercise training for patients with chronic atrial fibrillation," (Abstract) *Journal of Cardiopulmonary Rehabilitation*, 16 (3) at 193-6 (May-Jun. 1996).

Meyer K. et al., "Resistance exercise in comparison to bicycle ergometry. A study into the suitability of resistance training in exercise therapy for coronary patients," (Abstract) *Z. Kardiol.*, 81/10 at 531-537 (1992).

Meyer K. et al., "Can the training of coronary patients be monitored by readily measurable parameters?," (Abstract) *Herz*, 16 (4) at 215-6 (Aug. 1991).

Mineo K. et al., "Graded exercise in three cases of heart rupture after acute myocardial infarction," (Abstract) *American Journal of Physical Medicine and Rehabilitation*, 74 (6) at 453-7 (Nov.-Dec. 1995).

Mink B.D., "Pulmonary concerns and the exercise prescription," (Abstract) *Clinics in Sports Medicine*, 10 (1) at 105-16 Ref: 33 (Jan. 1991).

Moore R. Y., "A clock for the ages," Science, vol. 284 (Jun. 1999).

Neubauer B. et al., "Analysis of heart rate variations in patients with multiple sclerosis," *Journal of Neurology, Neurosurgery, and Psychiatry*, 41 at 417-419 (1978).

Oldridge N.B., "Carotid palpation, coronary heart disease and exercise rehabilitation," (Abstract) *Medicine and Science in Sports and Exercise*, 13 (1) at 6-8 (1981).

Otsuka Kuniaki et al., "Circadian rhythmic fractal scaling of heart rate variability in health and coronary artery disease", *Clinical Cardiology*, 20 at 631-638 (1977).

Pennisi, Elizabeth, "In Nature, Animals that Stop and Start Win the Race," *Science*, 288 at 83-85 (Apr. 7, 2000).

Petzinger, Jr. T., "Two doctors give new meaning to taking your business to heart," *The Wall Street Journal*, p. B1 (1999).

Przyklenk K. et al., "Regional Ischemic 'preconditioning' protects remote virgin myocardium from subsequent sustained coronary occulsion," *Circulation* vol. 87, No. 3 (Mar. 1993).

Ramazanoglu Y.M. et al., "Cardiorespiratory response to physical conditioning in children with bronchial asthma," (Abstract) *Pediatric Pulmonology*, 1 (5) at 272-7 (Sep.-Oct. 1985).

Redlin Uwe et al., "Exercise and human circadian rhythms: What we know and what we need to know," *Chronobiology International*, 14(2) at 221-119 (1997).

Reilly K. et al., "Differences between a supervised and independent strength and conditioning program with chronic low back syndromes," (Abstract) *Journal of Occupational Medicine*, 31 (6) at 547-50 (Jun. 1989).

Rousch Wade, "Can resetting hormonal rhythms treat illness?", *Science*, 269 at p. 1220-21 (1995).

Samitz G., "Aerobic upper body exercise. An unused potential in exercise therapy," (Abstract) *Wien. Med. Wochenschr.*, 142/14 at 309-313 (1992).

Schechtman V.L., "Dynamic Analysis of Cardiac R-R Intervals in Normal Infants Who Subsequently Succumbed to the Sudden Infant Death Syndrome," *Pediatric Research*, vol. 31, No. 6 at 606-612 (1992).

Schwartz Tony, "Making Waves. Can Dr. Irv Dardik's Radical Exercise Therapy Really Work Miracles," New York at 31-39 (Mar. 18, 1991).

Sparks K.E. et al., "Alternatives for cardiac rehabilitation patients unable to return to a hospital-based program," (Abstract) *Heart and Lung*, 22 (4) at 298-303 (Jul.-Aug. 1993).

Stephens R. et al., "Effects of self-monitored exercise on selected blood chemistry parameters of end-stage renal disease patients," (Abstract) *American Journal of Physical Medicine and Rehabilitation*, 70 (3) at 149-53 (Jun. 1991).

Stevens R. et al., "Comparison of supervised and unsupervised exercise training after coronary bypass surgery," (Abstract) *American Journal of Cardiology*, 53 (11) at 1524-8 (Jun. 1, 1984).

Tamiya N., "Study of physical fitness in children, and its application to pediatric clinics and sports medicine," (Abstract) Hokkaido Igaku Zasshi. *Hokkaido Journal of Medical Science*, 66 (6) at 849-67 (Nov. 1991).

Taniguchi K. et al., "Predischarge early exercise therapy in patients with acute myocardial infarction on the basis of anaerobic threshold (AT)," (Abstract) *Jpn. Circ. J.*, 54/11 at 1419-1425 (1990).

Todd I.C. et al., "Effect of exercise training on the total ischaemic burden: an assessment by 24 hour ambulatory electrocardiographic monitoring," (Abstract) *British Heart Journal*, 68 (6) at 560-6 (Dec. 1992).

Tsuji Hisako et al., "Reduced Heart Rate Variability and Mortality Risk In an Elderly Cohort, The Framingham Heart Study," *Circulation*, vol. 90, No. 2 at 878-883 (Aug. 1994).

Ueshima K. et al., "Management and evaluation of non-supervised home exercise program in a convalescent phase of acute myocardial infarction," (Abstract) *Japanese Circulation Journal*, 54 (11) at 1437-42 (Nov. 1990).

van Dixhoorn J. et al., "Physical training and relaxation therapy in cardiac rehabilitation assessed through a composite criterion for training outcome," (Abstract) *American Heart Journal*, 118 (3) at 545-52 (Sep. 1989).

Waddington J.L. et al., "Resting heartrate variability in man declines with age," *Experience*, 35 at 1197-1198 (1979).

Wheeler Timothy et al., "Cardiac Denervation in Diabetes," *British Medical Journal*, 4 at p. 584-586 (Dec. 8, 1973).

Williams L.R. et al., "Vascular rehabilitation: benefits of a structured exercise/risk modification program," (Abstract) *Journal of Vascular Surgery*, 14 (3) at 320-6 (Sep. 1991).

Williams M.A. et al., "Guidelines for exercise therapy of the elderly after myocardial infarction," (Abstract) *Eur. Heart J. 5, Supplement E* at 121-123 (1984).

Williams, Terrie M. et al., "Sink or Swim: Strategies for Cost-Efficient Diving by Marine Mammals," *Science* 288 at 133-136 (Apr. 7, 2000).

Wolfe L.A. et al., "Prescription of aerobic exercise during pregnancy," (Abstract) *Sports Medicine*, 8 (5) at 273-301 Ref: 133 (Nov. 1989).

Wright N.C. et al., "Aerobic walking in slowly progressive neuromuscular disease: effect of a 12-week program," (Abstract) *Archives of Physical Medicine and Rehabilitation*, 77 (1) at 64-9 (Jan. 1996).

Yellon, Derek M. et al., "A 'Second Window of Protection' or Delayed Preconditioning Phenomenon: Future Horizons for Myocardial Protection?," *J. Mo. Cell Cardiol.* 27 at 1023-1034 (1995).

Yellon, Derek M. et al., "Ischaemic preconditiong; present position and future directions," Cardiovascular Research, 37 at 21-33 (1998).

\* cited by examiner

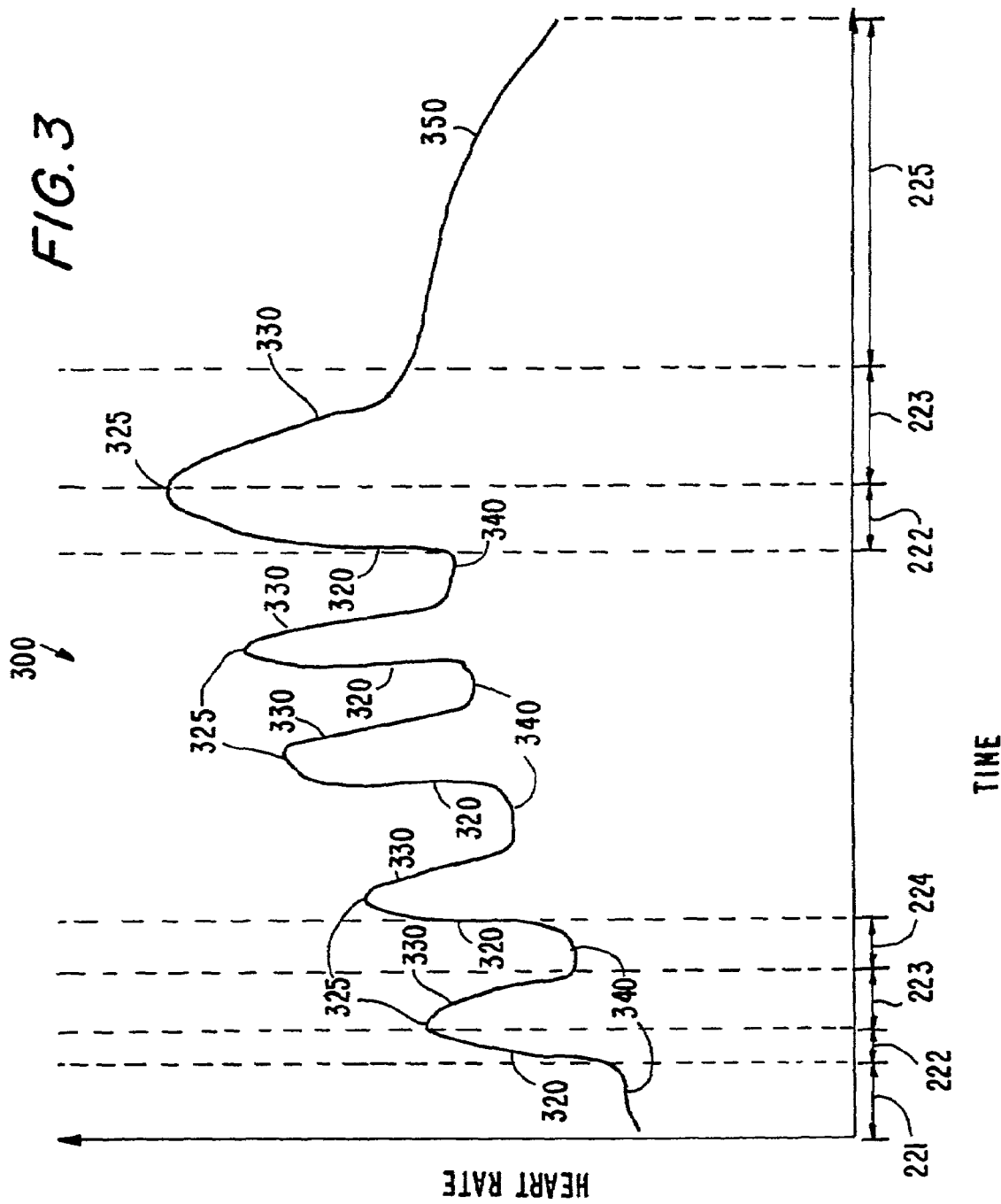

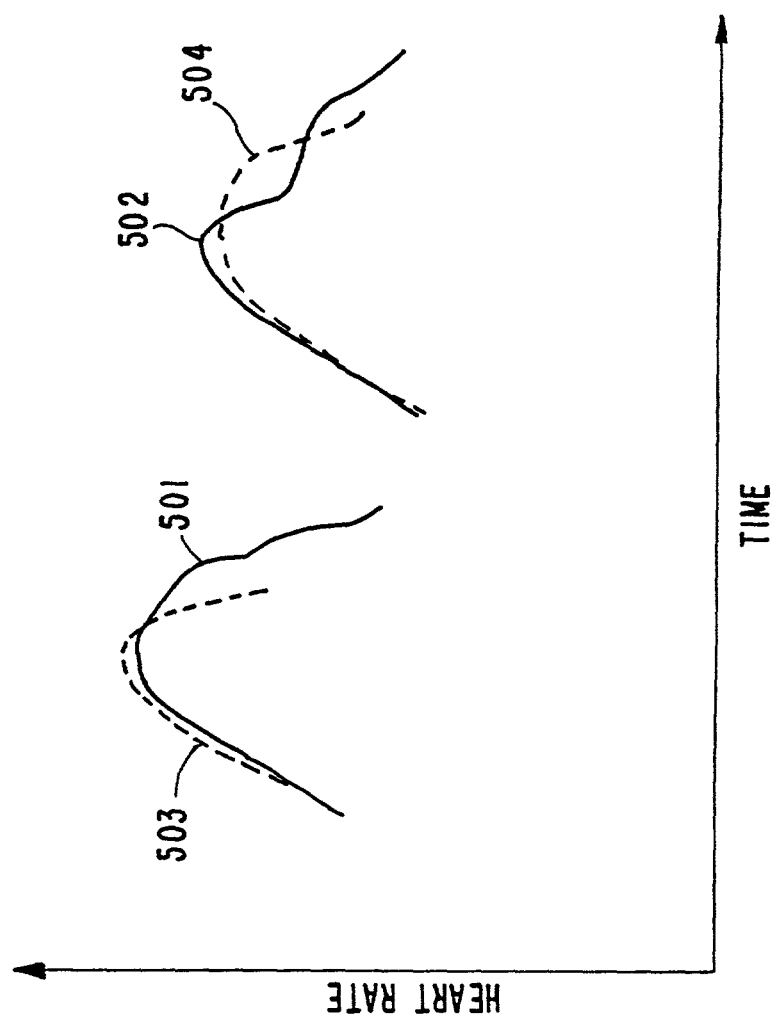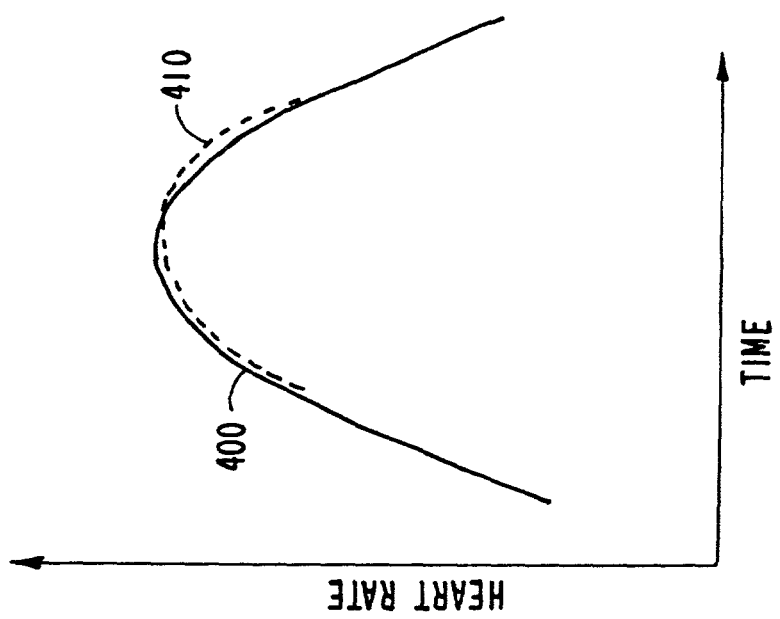

REGIMEN beginning April 25

115's — 810

6-9 AM

| Tue Apr 25 | Thu Apr 27 | Sun Apr 30 | Tue May 2 |
|---|---|---|---|
| 94 | 98 | 100 | 102 |
| 103 | 109 | 107 | 109 |
| 111 | 114 | 112 | 116 |
| 114 | 5 minute break | 115 | 117 |
| 10 minute break | 111 | 119 | 122 |
| 108 | 117 | | |
| 115 | 120 | | |
| 118 | | | |

9-12 AM

| Thu May 4 | Sun May 7 | Tue May 9 | |
|---|---|---|---|
| 104 | 108 | 111 | |
| 114 | 116 | 118 (s) | |
| 118 (s) | 122 (s) | 124 (s) | |
| 122 | | | |

3-6 PM

| Thu May 11 | Sun May 14 | Tue May 16 | Thu May 18 |
|---|---|---|---|
| 106 | 110 | 113 | 115 |
| 115 | 118 (s) | 118 (s) | 121 (s) |
| 119 | 121 (s) | 121 (s) | 130 (s) |
| 123 (s) | 124 (s) | 122 (s) | |
| 120 (s) | | 130 (s) | |
| 124 | | | |

Rest Week

FIG. 8

SYSTEMS AND METHODS FOR ASSESSING AND MODIFYING AN INDIVIDUAL'S PHYSIOLOGICAL CONDITION

This application claims priority from U.S. patent application Ser. No. 09/609,087, filed Jun. 30, 2000, which is now abandoned.

BACKGROUND OF THE INVENTION

This invention relates generally to systems and methods for assessing and modifying an individual's physiological condition. More particularly, this invention relates to systems and methods for assessing and modifying an individual's physiological condition by analyzing heart rate data collected while the individual is exercising according to an exercise regimen.

The human physiological condition is the result of complex interactions between various underlying phenomena that are internal as well as external to the human body. For example, cardiac activity is an accumulation of complex interactions between various internal phenomena such as muscular, neurological, vascular, pulmonary, endocrinal, chemical, and cellular phenomena. Cardiac activity also responds to external behavioral activity, such as physical activity that causes energy expenditure and recovery, and to naturally occurring environmental phenomena, such as day-night cycles, lunar cycles, and weather seasons.

A perspective view of human physiology enables one to describe physiological functions in terms of wave phenomena made up of a superposition of other underlying wave phenomena. For example, cardiac activity manifests itself through repetitive pulsations of the heart as a heart wave. The heart wave is a result of a superposition of many underlying waves (i.e., cycles) including behavioral waves (e.g., energy expenditure and recovery cycles in response to physical activity), environmental waves (e.g., day-night cycles), and internal waves (e.g., molecular biological, cellular, and chemical cycles).

Heart rate variability (i.e., the variation in an individual's heart rate) is another manifestation of the superimposed effects of various endogenous and exogenous phenomena on human physiology. Decreased heart rate variability has been associated with abnormal physiological conditions and increased mortality. Treatments which increase heart rate variability in an individual's serve both therapeutic as well as prophylactic purposes. Dardik U.S. Pat. Nos. 5,007,430, 5,800,737, 5,163,439, and 5,752,521, which are hereby incorporated by reference in their entireties, further elaborate on the wave nature of cardiac activity.

Current methods for analyzing cardiac activity, however, are inadequate because they do not analyze the cyclical properties of heart waves with a view to unraveling details of their superimposed wave structure. In the absence of quantitative information on the cyclical properties of heart waves, it is difficult to provide a complete or accurate assessment of an individual's physiological condition, and individually tailor exercise regimens. For example, most methods of prescribing exercise regimens are often based on general criteria, such as age, rather than an individual's actual physiological condition.

It would therefore be desirable to have systems and methods that more completely and quantitatively characterize heart waves.

It would further be desirable to characterize heart waves in a manner that provides an accurate quantitative metric of an individual's physiological condition.

It would also be desirable to be able to generate individually tailored exercise regimens for modifying an individual's physiological condition, based on a quantitative metric.

SUMMARY AND OBJECTS OF THE INVENTION

It is an object of the present invention to provide systems and methods for-a detailed characterization of heart waves that enables a relatively complete assessment of an individual's physiological condition.

It is a further object of the present invention to provide quantitative metrics of an individual's physiological condition, based on detailed characterization of cyclic properties of heart waves.

It is also an object of the present invention to provide systems and methods for generating individually tailored exercise regimens that are independent of general criteria, such as age, but are based on more experimentally determined metrics.

It is a still further object of the present invention to provide systems and methods for generating individually tailored exercise regimens based on these metrics, with a goal of increasing heart rate variability.

These and other objects of the invention are accomplished in accordance with the principles of the present invention by providing systems and methods for assessing an individual's physiological condition by extracting cycle parameters from a recorded time trace of heart rate data collected while an individual is exercising according to an exercise regimen. While exercising, the individual's heart wave includes energy expenditure and recovery cycles in response to cycles of physical activity. The cycle parameters containing relevant information can include discrete parameters and shape specific parameters. Discrete parameters include, for example, maximum, minimum, and resting heart rates, as well as upward, downward, and baseline slopes. The shape specific parameters (discussed below) can be used to characterize the shapes of portions of the time trace that are believed to contain physiologically important information. Based on these parameters, an individual's physiological condition can be quantified (e.g., in a heart wave index or a capacity index), which can incorporate some or all of the relevant physiological information contained in a time trace.

The quantitative figure of merit can be used to gauge the progress of an individual under an exercise regimen and to design individually tailored exercise regimens for modifying the individual's physiological condition. When used, exercise regimens modify the individual's condition by shaping the heart wave with a goal of increasing the individual's heart rate variability. Individualized heart wave shaping can be achieved in accordance with this invention by application of the principles for therapeutic treatment and bio-rhythmic feed back taught by Dardik, U.S. Pat. Nos. 5,800,737, 5,752,521, 5,163,439, and 5,007,430.

According to one embodiment of the present invention, an exercise regimen having at least one exercise session that contains one or more exercise cycles is used for assessing an individual's physiological condition. The individual's heart rate is monitored during the exercise session, and a time trace of the heart rate is recorded in an electronic file. Then, the time trace is analyzed to determine one or more cycle parameters, such as a peak heart rate, a minimum heart rate, a resting heart rate, and a base line slope. These parameters can then be used to determine a heart wave index indicative of the individual's physiological condition.

Additional parameters, such as parabolic coefficients, which characterize the shape of one or more portions of the time trace, can also be obtained. These parameters can also be incorporated into the heart wave index or another figure of merit.

According to another aspect of this invention, a quantitative determination of an individual's physiological condition or capability can be used to prescribe an exercise regimen. In one embodiment of this invention, an individual is subject to an exercise test to determine an initial physiological capability. During the test the individual's heart rate is monitored and preferably stored in the form of an electronic file. The test typically includes at least one, and preferably several exercise cycles, including a maximum effort cycle in which the individual attempts to exercise to the individual's maximum capability. Cycle parameters are then obtained by analyzing the heart rate data. The cycle parameters (such as those that characterize the maximum effort cycle) can be incorporated into a figure of merit. Then, an individualized exercise regimen can be generated using an algorithm that relates the figure of merit, or the cycle parameters directly, to exercise regimens.

In accordance with the principles of the present invention, a system for assessing an individual's physiological condition or capability includes at least an electronic monitor, a recorder, and an analyzer. The monitor monitors the individual's heart rate. The recorder records a time trace of the individual heart rate in an electronic file. The analyzer analyzes the electronic file, using one or more routines (i.e., procedures, programs, or algorithms) to, for example, determine at least one cycle parameter, such as a peak heart rate, a maximum heart rate, a minimum heart rate, an upward slope, a downward slope, and a base line slope. The analyzer can derive shape parameters by fitting one or more parabolas or other mathematical models to portions of the time trace, and can determine a figure of merit based on the determined cycle parameters.

According to another aspect of this invention, electronic networks, such as the Internet, can be used to receive data and provide information to the individual remotely.

BRIEF DESCRIPTION OF THE DRAWINGS AND THE APPENDIX

The above and other objects and advantages of the present invention will be apparent upon consideration of the following detailed description, taken in conjunction with the accompanying drawings, in which like reference characters refer to like parts throughout, and in which:

FIG. 3 is an illustrative time trace of heart rate data collected over an exercise session, in accordance with the present invention;

FIG. 4 is an illustrative top portion of a cycle in a time trace including an illustrative theoretical parabola that has been fit thereto in accordance with the present invention;

FIG. 5 shows two illustrative top portions of a time trace, each corresponding to an abnormal physiological condition, including two illustrative theoretical parabolas that have been fit thereto, in accordance with present invention;

FIG. 8 is an illustrative exercise regimen that has been generated in accordance with the present invention;

DETAILED DESCRIPTION OF THE INVENTION

In order that the invention herein described can be fully understood, the following detailed description is set forth.

Figure 1:
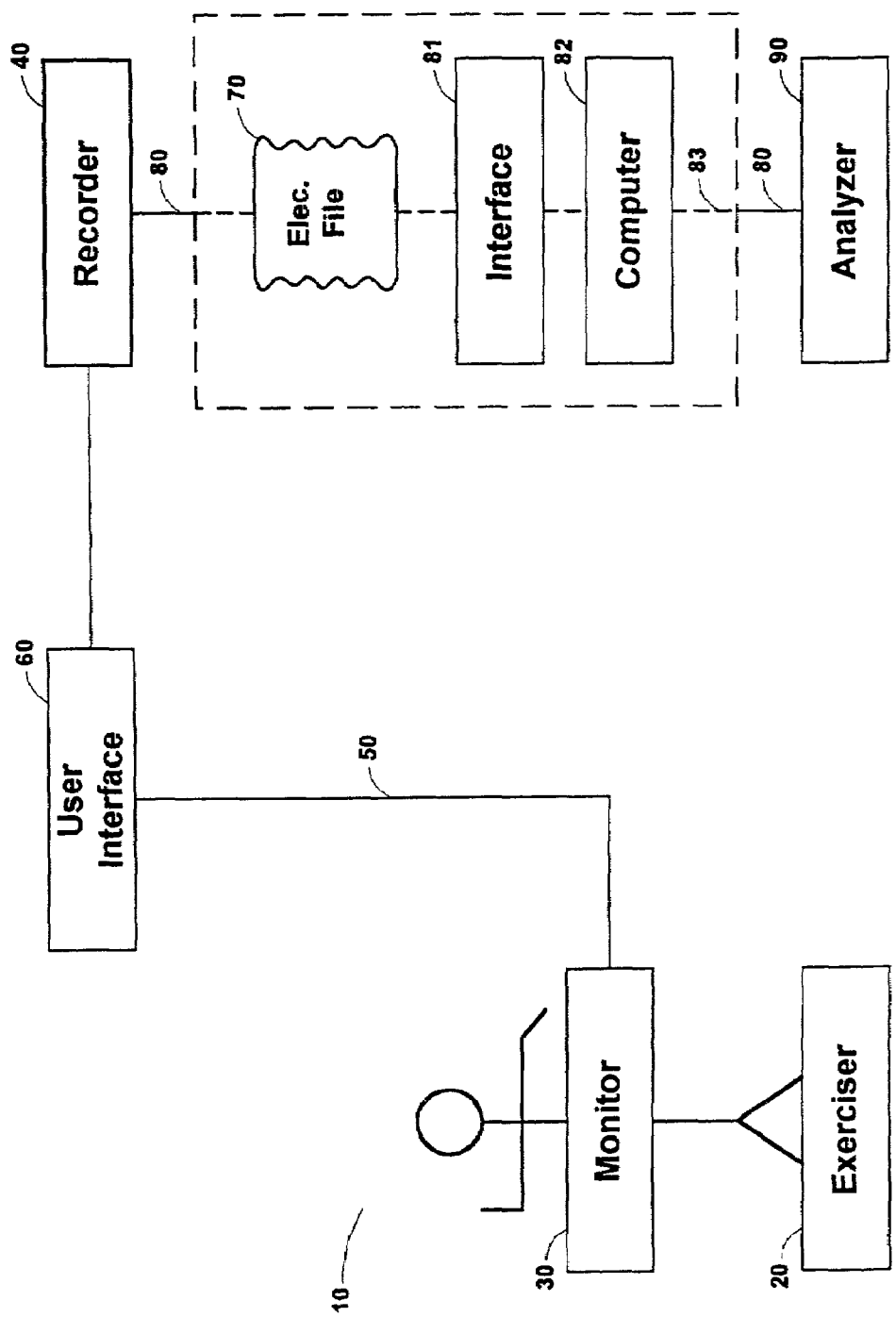
FIG. 1 is a schematic block diagram of an illustrative system constructed in accordance with the present invention.

FIG. 1 shows illustrative systems for assessing an individual's physiological condition during performance of an exercise regimen. Individual 10 is shown exercising on exerciser 20. Exerciser 20, for example, can be a treadmill machine, a trampoline, a stationary bicycle, or any other suitable exercising apparatus. Exerciser 20, however, is optional because exercise can be done without the aid of an exercise apparatus (e.g., running, jogging, jumping, walking, moving arms and shoulders, or swinging legs). Electronic monitor 30 monitors the heart rate of individual 10.

Monitor 30 can be any commercially available unit that measures the heart rate and transmits heart rate data to recorder 40 through link 50. Link 50 can be, for example, a magnetic coupling, a wireless transmission system, or any other electronic or electromagnetic network. Monitor 30 can be connected through link 50 to user interface 60. Interface 60 can provide to users visual, auditory, or tactile information regarding the heart rate or any other type of data. Recorder 40 can be, for example, a printer, a chart recorder, or other device (or combination of devices) that can record the time trace in an electronic file 70.

Monitor 30, recorder 40, link 50, and interface 60 can be obtained commercially as an integrated heart monitoring and recording unit (such as Model Polar M52 or Model Polar NV sold under the trademark POLAR™, by Polar Electro Inc., of Woodbury, N.Y.). Link 80 connects recorder 40 to analyzer 90, and can be local or remote to exerciser 20. According to one embodiment, and as shown in FIG. 1, link 80 can include watch reading interface 81 (such as "Polar Advantage Interface System" Model 900622K sold under the under the trademark POLAR™, also by Polar Electro Inc.), personal computer 82, and Internet link 83. It will be appreciated, however, that link 80 can be any electronic network that couples recorder 40 to analyzer 90 for data communication.

Analyzer 90 can include one or more electronic computing devices, preferably programmable computing devices (such as Model HP-VEE sold by Hewlett Packard Company, of Palo Alto, Calif.). It will be appreciated that analysis could, in some cases, involve manual computation or review. Analyzer 90 analyzes electronic file 70, which contains at least one time trace of the heart rate, to determine at least one exercise cycle parameter (e.g., a maximum heart rate). Based on that parameter, analyzer 90 can calculate a heart wave index indicative of the individual's physiological condition.

Figure 2:
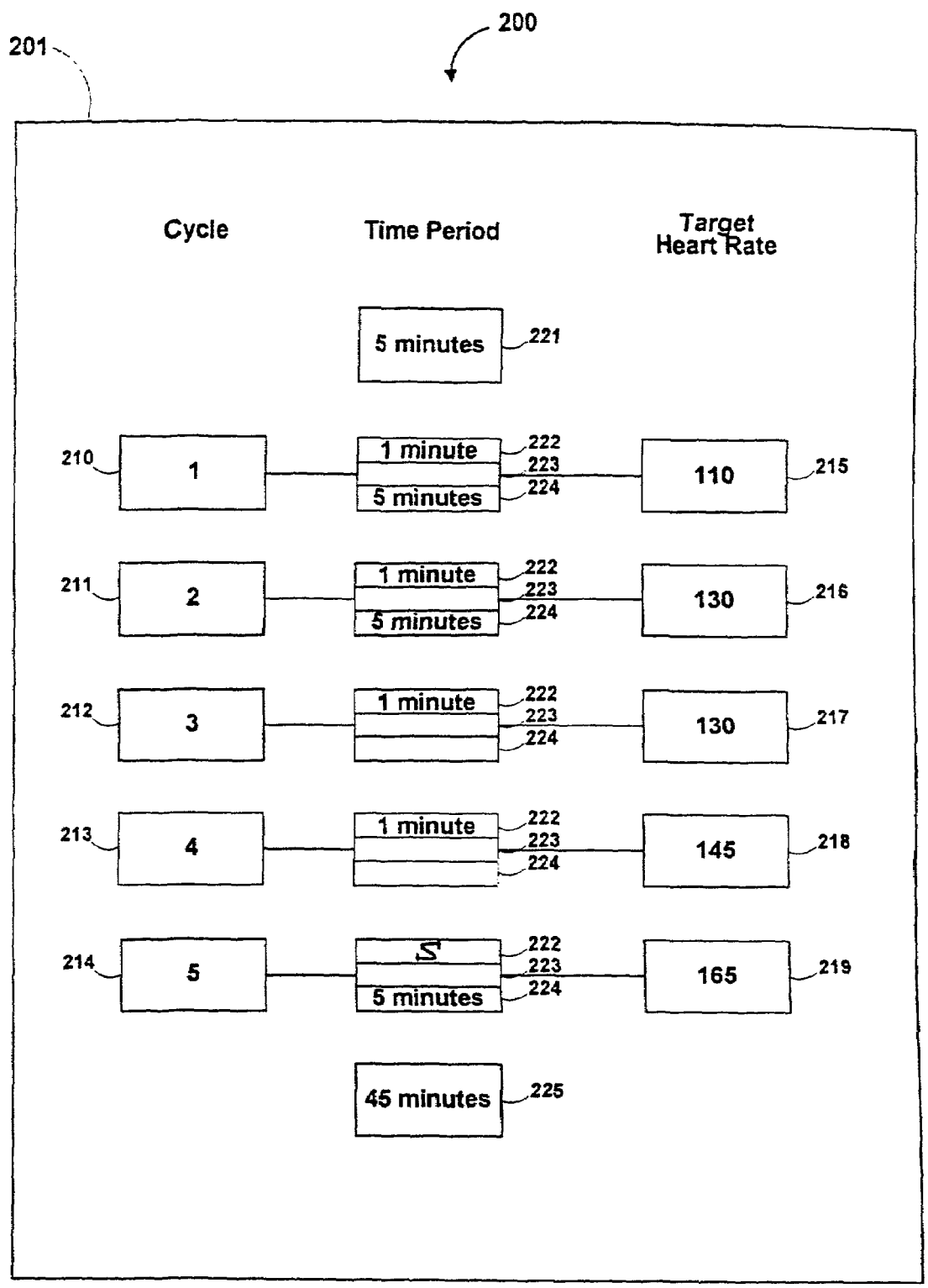
FIG. 2 is an illustrative exercise regimen that can be generated and used in accordance with the present invention.

FIG. 2 shows illustrative exercise regimen 200, which includes exercise session 201. FIG. 3 shows corresponding illustrative time trace 300 of an individual's heart rate, when exercising according to session 201. Exercise session 201 includes five successive exercise cycles 210–214 of increasing difficulty with each of cycles 210–214 associated with generally increasing target heart rates 215–219. It will be appreciated that an exercise session according to this invention could include more or less than five cycles and that the target heart rates need not increase monotonically.

In each of exercise cycles 210–214, the individual is expected to commence physical activity and continue the activity over first time period 222 in an attempt to raise the heart rate to one of respective target heart rates 215–219. Period 222 can be fixed or variable. Preferably, period 222 is variable but has an upper time limit. When period 222 is variable and has an upper time limit (e.g., variable cycle 214), the individual exercises only until either the target heart rate is reached or the upper time limit is reached. Preferably, the upper time limit is about one minute. However, when period 222 is fixed, the individual exercises for a fixed amount of time even if the individual's heart rate goes over or stays under the target heart rate. Period 222 when fixed is preferably between about 30 seconds and about 90 seconds, and more preferably about one minute (e.g., cycles 210–213).

One type of variable cycle is a spike cycle. In spike cycle 214 (represented as "S"), an individual exercises as vigorously as possible to reach target heart rate 219 in as short a time as possible. Thus, the actual time period depends on the condition of the individual.

In each cycle 210–214, after initial period 222, the individual relaxes during time period 223 by gradually diminishing, or preferably, by abruptly ceasing physical activity. Period 223 can also be fixed or variable. Preferably, period 223 is variable and ends when the heart rate substantially stabilizes (i.e., levels off). A heart rate can be considered "stabilized" when the heart rate changes less than a certain amount over a pre-determined period of time. For example, a heart rate can be considered to be stabilized when the heart rate changes less than about 3 beats/min. over an interval, such as a one minute interval.

Exercise session 201 can include intervening rest periods 224 between successive exercise cycles 210–214. Additional intervening rest period 224 can also be inserted before post-exercise recovery period 225. Rest periods 221, 224, and 225 can have fixed durations or can be determined by the individual's performance by the amount of time required for the heart rate to substantially stabilize.

A time trace can contain heart rate data collected over any time period ranging, for example, from a few seconds to several days. Thus a time trace can include data collected over a single or multiple exercise cycles, sessions, or regimens. FIG. 3 shows illustrative time trace 300 of an individual's heart rate during exercise session 201. Trace 300 includes pre-exercise portion 310, which represents the heart rate during time period 221. During period 221, the individual can stay still, acclimatize to exerciser 20 and surroundings, and allow the heart rate to stabilize over several minutes before commencing an exercise cycle. Portion 310 is believed to contain information on the individual's resting heart rate and can serve as a reference or base line heart rate from which to assess changes in the individual's physiological condition, for example, due to exercise.

Each of portions 320 represents a rising heart rate during each of time periods 222 (FIG. 2). It is believed that each of portions 320 contains physiological information on the individual's ability to sustain increasing stress.

Each of portions 330 represents a portion of an exercise cycle in which the heart rate of the individual falls. The heart rate often exhibits a natural overshoot phenomena at the end of portion 330, typically falling below an initial base line heart rate (prior to cycles 210–214). After overshooting, the heart rate normally recovers to a new base line heart rate. Portion 330 is believed to contain physiological information on the individual's short term ability to recover from stress.

Each of top portions 325 represents the heart rate as it transitions between periods 222 and 224, which roughly correspond to time trace portions 320 and 330. In each of cycles 210–214, the individual attains a peak (i.e., maximum) heart rate during top portion 325. Peak heart rates have been found to be a significant measure of an individual's physiological condition.

Each of portions 340 represents the heart rate during stabilizing periods 224 which allow the individual's heart rate to stabilize between cycles 210–214. Portions 340 are believed to contain physiological information on shifts in the resting heart rates to new base line levels in response to exercise cycles 210–214.

Portion 350 represents the heart rate during post-exercise recovery period 225. Portion 350 is believed to contain physiological information on an individual's ability to recover from the cumulative effects of exercise cycles 210–214, including any shift in base line heart rates.

An assessment of an individual's physiological condition can be quantified in a figure of merit (e.g., a heart wave index). This figure can incorporate some or all of the relevant physiological information contained in a time trace of the heart rate, including any of the cycle parameters discussed herein. A heart wave index, for example, is a single metric that can be used to summarize an assessment of the physiological condition. The heart wave index can also be regularly determined and used to gauge the progress of an individual under an exercise regimen. Use of one or more quantitative figures of merit enables an accurate determination of causes and effects of changes that occur in an individual's physiological condition based on an exercise routine. As explained more fully below, exercise regimens for an individual can be designed to cause specific changes in an individual's heart wave index.

Information contained in a time trace can be characterized by cycle parameters (such as peak heart rates, minimum heart rates, upward slopes and downward slopes), that are achieved during one or more exercise cycles in an exercise regimen. Other cycle parameters such as baseline slopes and resting heart rates can be used to characterize pre-exercise, intervening, and post-exercise rest periods.

Information contained in a time trace can be further characterized by shape specific cycle parameters that describe the shapes of portions of the time trace. These shape parameters can be incorporated into the heart wave index. For example, cycle parameters that describe the parabolicity of a top portion or a rest portion can be used to determine a heart wave index. Moreover, multiple shape parameters can be used in combination. For example, parabolic coefficients can be used in combination of baseline slopes.

A time trace can be analyzed to determine a maximum heart rate achieved by the individual in the course of an exercise session. According to one embodiment of the present invention this maximum rate serves as the heart wave index that is used to determine the target heart rates in an individually tailored exercise regimen.

Figure 3A:
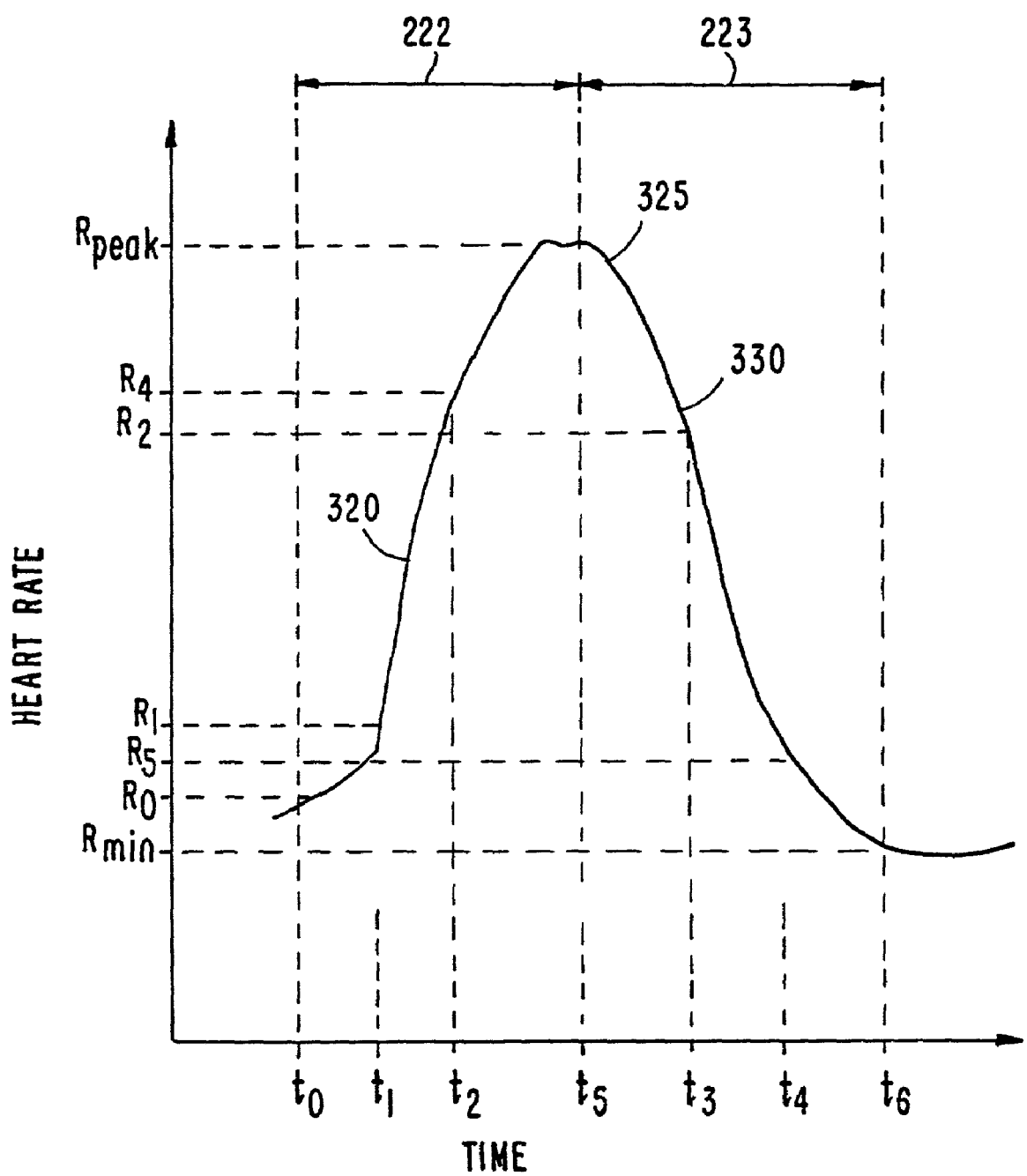
FIG. 3a is an illustrative time trace of heart rate data collected over an exercise cycle, in accordance with the present invention.

A time trace can be further analyzed to determine other cycle parameters, such as an upward slope $S_{up}$, a downward slope $S_{down}$ a peak heart rate $R_{peak}$, and a minimum heart rate $R_{min}$. FIG. 3a shows an illustrative cycle 214 of time trace 300. Starting heart rate $R_0$ is determined by finding the heart rate at time $t_0$, at or about the start of period 222. Peak heart rate $R_{peak}$ and corresponding time $t_5$ are determined by finding the highest heart rate datum within top portion 325. Time $t_5$ is often located at or about the end of period 222 by which time the target heart rate has been reached. Minimum heart rate $R_{min}$ and corresponding time $t_6$, are determined by finding the lowest heart rate datum in portion 330. Time $t_6$ is often located at or about the end of period 223 by which time the heart rate has stabilized.

The upward slope can be calculated as a derivative, for example, using the change in the heart rate from $R_0$ to $R_{peak}$ over all of portion 320 (corresponding to time period 222), substantially according to:

$$S_{up}=(R\text{peak}-R_0)/(T_5-t_0)$$

The downward slope can also be calculated as a derivative, for example, using the change in the heart rate from $R_{peak}$ to $R_{min}$, substantially according to:

$$S_{down}=(R\text{peak}-R_{min})/(t_6-t_5)$$

It will be appreciated that other formulations of the upward and downward slope can be used in accordance with the present invention. For example, an upward slope can be calculated by first identifying a segment of portion 320 which is substantially linear. Such a substantially linear portion is shown in FIG. 3a as the segment between heart rates $R_1$ and $R_2$, corresponding to times $t_1$ and $t_2$, respectively. Upward slope $S_{up}$ can be calculated according to:

$$S_{up}=(R_2-R_1)/(t_2-t_1)$$

Similarly, downward slope $S_{down}$ can be calculated by identifying a segment of portion 330 which is substantially linear, such as the segment between heart rates $R_4$ and $R_5$ corresponding to times $t_3$ and $t_4$, respectively. Downward slope $S_{down}$ can be calculated according to:

$$S_{down}=(R_4-R_5)/(t_4-t_3)$$

A heart wave index can be determined using one or more of these cycle parameters. For example, heart wave index HWI can be defined as a weighted sum of at least two of upward slope $S_{up}$, downward slope $R_{down}$, peak heart rate $R_{peak}$, and minimum heart rate $R_{min}$, for example, according to:

$$HWI=a\,R_{peak}+b\,S_{up}+c\,S_{down}+d\,R_{min}$$

where a, b, c and d are weight factors that can be positive, zero, or negative numbers.

For example, a heart wave index can be a straight linear sum of upward slope $S_{up}$, downward slope $S_{down}$ and peak heart rate $R_{peak}$. In this case, weight factors a, b, and c set are equal to 1, and factor d is equal to zero:

$$HWI=R_{peak}+S_{up}+S_{down}$$

It will be appreciated that any convenient formulation could be used, depending on the nature or properties of the particular quantities being measured.

A heart wave index could also incorporate one or more other cycle parameters that characterize pre-exercise, intervening and post-exercise rest portions determined from the time trace. For example, resting heart rate $R_{rest}$ can be used to characterize any of rest portions 310, 340, and 350. Resting heart rate $R_{rest}$ can be determined, for example, by averaging the heart rate after it has substantially stabilized. Further, for example, a base line slope $S_{base}$ can be used to characterize any one or any combination of rest portions. (A combination of rest portions can, for example, consist of all of portions 310, 340, and 350). Base line slope $S_{base}$ can be calculated by determining the change in the heart rate during one or more rest portions, in a manner analogous to the determination of upward and downward slopes described above.

Thus, the heart wave index can be any function of cycle parameters:

HWI=function (cycle parameters).

A heart wave index can be equal, for example, to the difference in the resting heart rates determined from portions 310 and 350.

Figure 9:
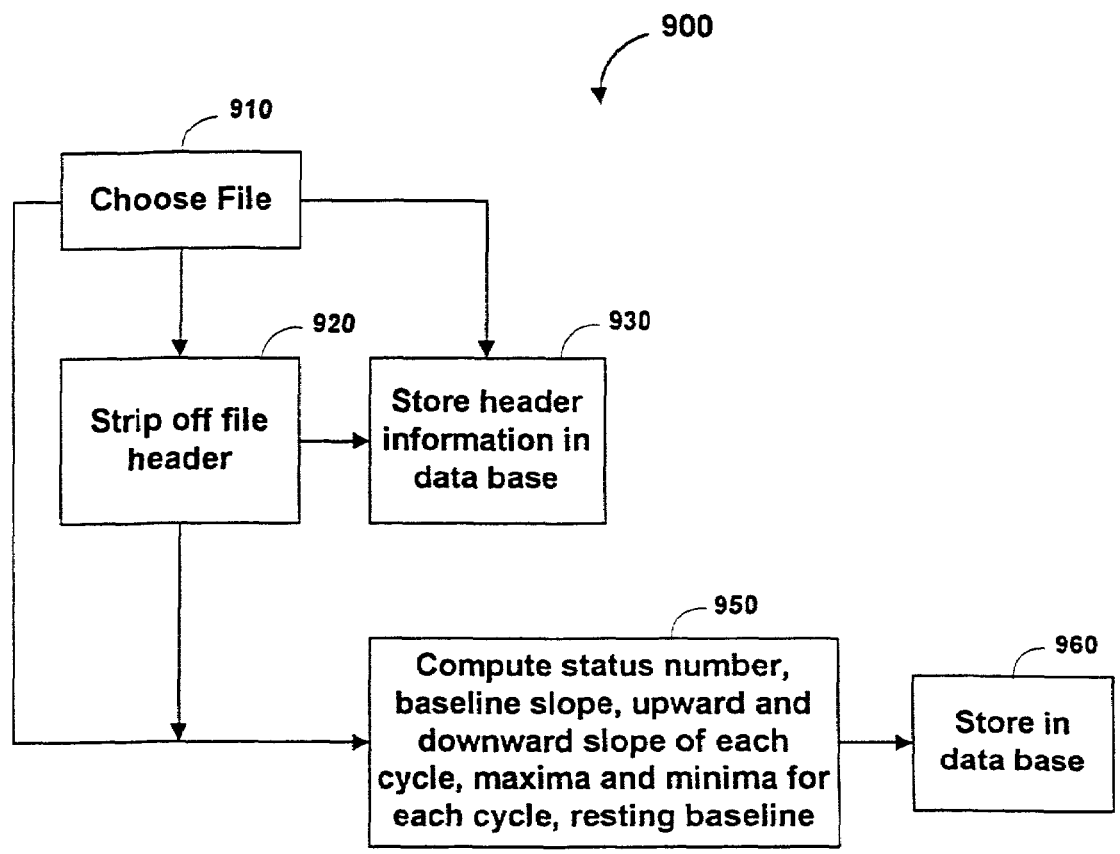
FIG. 9 is a flow chart of a process used to extract cycle parameters from a time trace, in accordance with the present invention.

FIG. 9 shows a flow diagram of process 900 of one embodiment used to analyze a time trace contained in an electronic file. Process 900 begins at step 910 by selecting or receiving an electronic file for analysis. Next, in step 920, any file headers attached to the electronic file can be stripped away. In step 930, any header information can be stored in a database. Steps 920 and 930 are optional, but can be useful when the file is received in the form of an e-mail, for example.

In step 950, the time trace is further analyzed by determining various cycle parameters, such as baseline slope, upward and downward slopes, and/or maxima and minima for each cycle. In addition to determining cycle parameters, a heart wave index can also be calculated in step 950. In step 960, analysis results are optionally stored in a data base.

Shape parameters can also be derived from the time trace, for example, by fitting one or more top portions 325, or through all of rest portions 310, 340 and 350 with a theoretical parabola, $$y=Ax^2+Bx+C.$$

Regression analysis techniques can be used to fit the parabola to obtain coefficients A, B, and C. Any suitable statistical test (e.g., chi-square) can be used to determine the quality of the fit. At least one goodness of fit parameter (e.g., coefficient of correlation R, or coefficient of determination $R^2$) that characterizes the quality of the fit can also be calculated.

FIG. 4 illustrates how a parabola can be fit to a top portion, such as top portion 325, to obtain one or more shape parameters. Time trace portion 400 represents a top portion of an exercise cycle. Theoretical parabola 410 represents a best fit generated, for example, by regression analysis. The heart wave index can then be determined using any of the cycle parameters and one or more shape parameters, such as the parabolic coefficients and one or more goodness of fit parameters. The heart wave index can itself be equal to a goodness of fit parameter.

Figure 10:
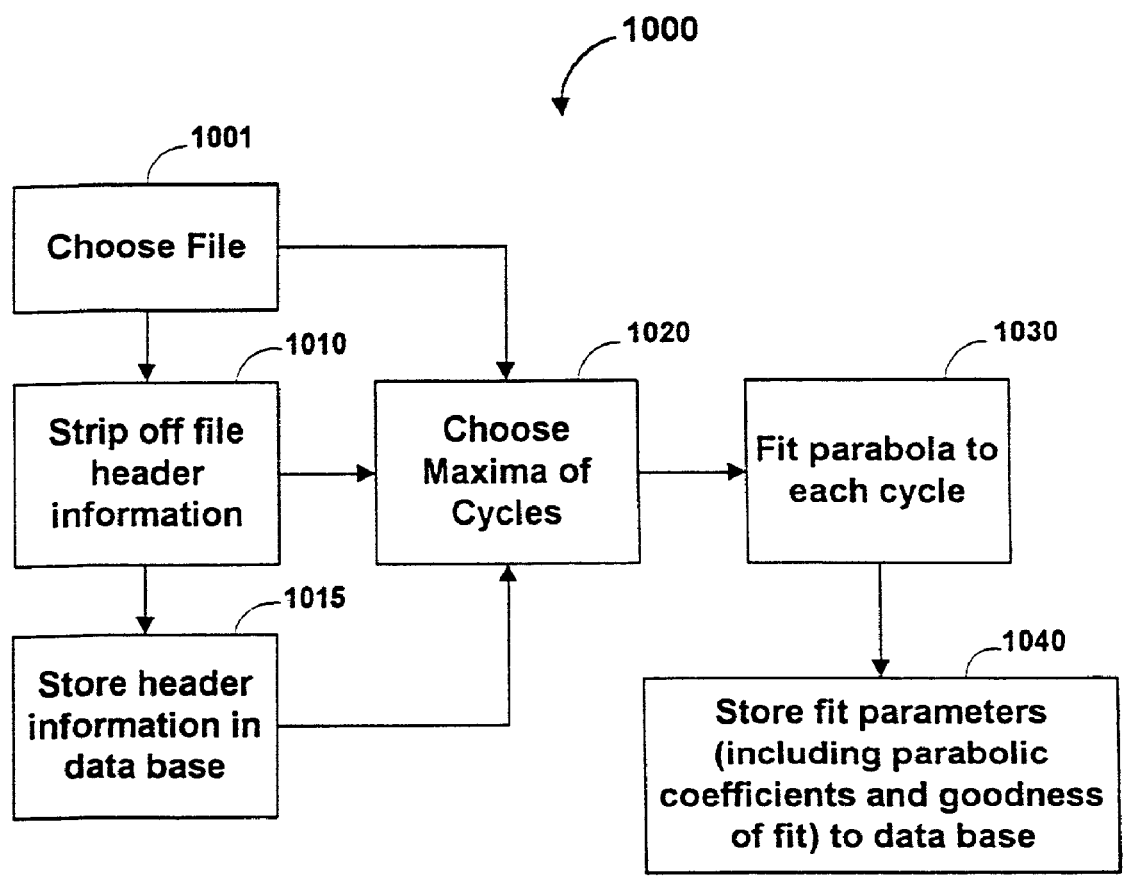
FIG. 10 is a flow chart of a process used to extract shape parameters from top portions of a time trace, in accordance with the present invention.

FIG. 10 shows a flow diagram of process 1000 of one embodiment used to fit a parabola to top portions contained in an electronic file. In step 1001, an electronic file to be analyzed is selected or received. Next, any file headers attached to the electronic file can be stripped. In step 1020, a maximum heart rate for each relevant cycle is determined, which could involve locating the top portion of each cycle. In step 1030, the top portions are fit to theoretical shapes (e.g., parabolas) using, for example, regression analysis.

Parabolic coefficients are obtained and at least one goodness of fit parameter is preferably calculated for each fit. In step 1040, analysis results can optionally be stored in a data base.

Figure 11:
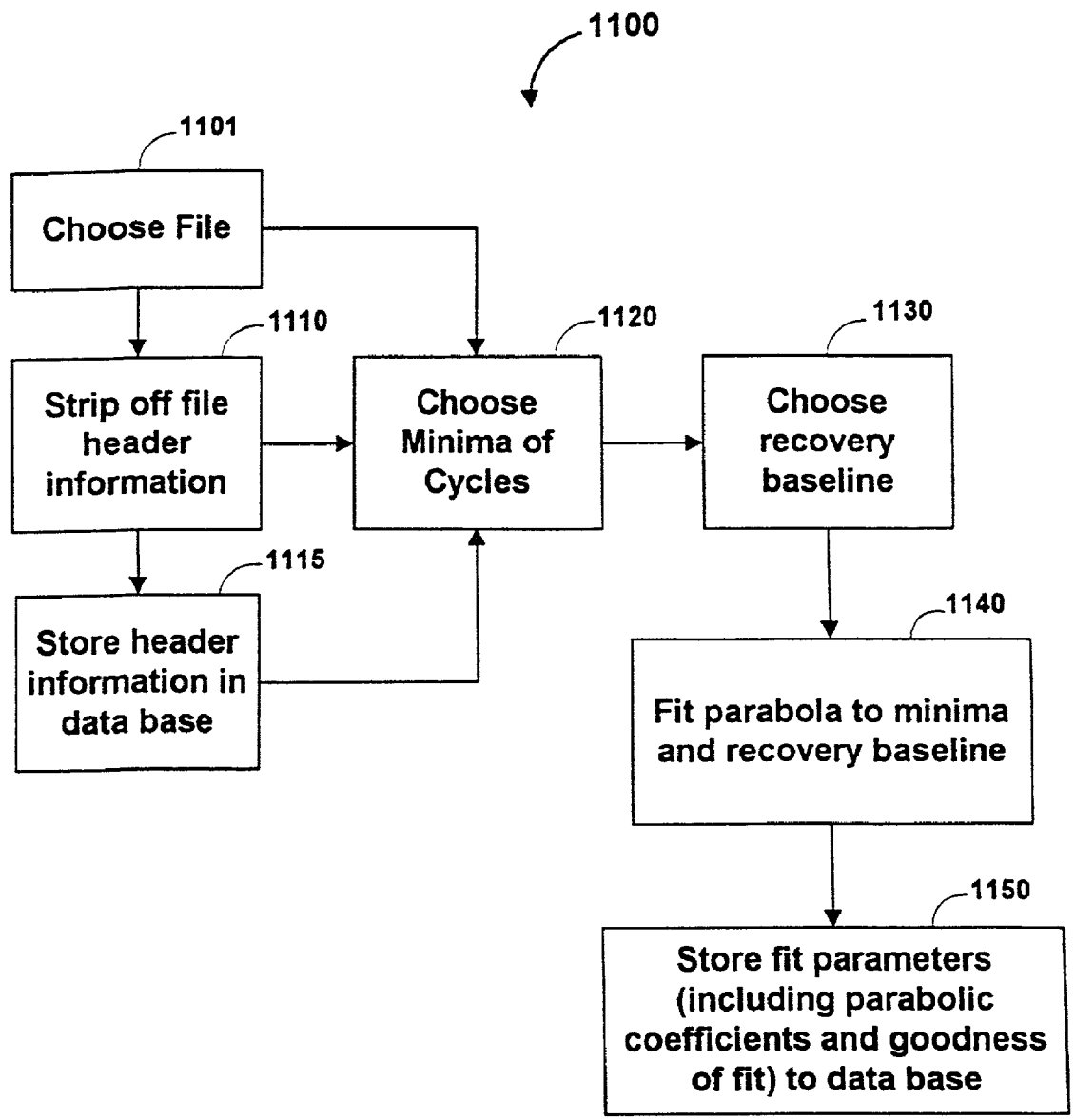
FIG. 11 is a flow chart of a process used to extract shape parameters from rest portions of a time trace, in accordance with the present invention; and Appendix A contains actual exercise regimens appropriate for individuals with nominal capacity indices ranging from 120 to 180 units, in accordance with this invention.

Similarly, FIG. 11 shows a flow diagram of process 1100 of one embodiment used to fit a parabola to resting portions in a time trace. In step 1101, an electronic file to be analyzed is selected or received. In step 1110, any file headers attached to the electronic file can be stripped away and optionally stored. In step 1120, a minimum heart rate for each cycle is determined. In step 1130, a recovery baseline is chosen. This can involve determining a portion of the time trace in which the heart rate is stabilized after recovering from a minimum determined in step 1120. In this manner, rest portions 340 corresponding to each cycle can be identified. In step 1140, regression analysis or any other type of comparable analysis routines are used to fit a parabola to each rest portion. For each fit, parabolic coefficients and/or at least one goodness of fit parameters can be obtained. In step 1150, analysis results can be optionally stored in a data base.

As explained above, the shapes of the top portions and the resting portions are believed to contain information on the physiological condition of the individual. In particular, it has been discovered that abnormal physiological conditions are often associated with non-parabolic shapes. FIG. 5 shows a heart rate trace that includes two illustrative top portions 501 and 502. These portions correspond to abnormal physiological conditions because their shapes deviate strongly from symmetric parabolas 503 and 504, respectively.

Figure 6A:
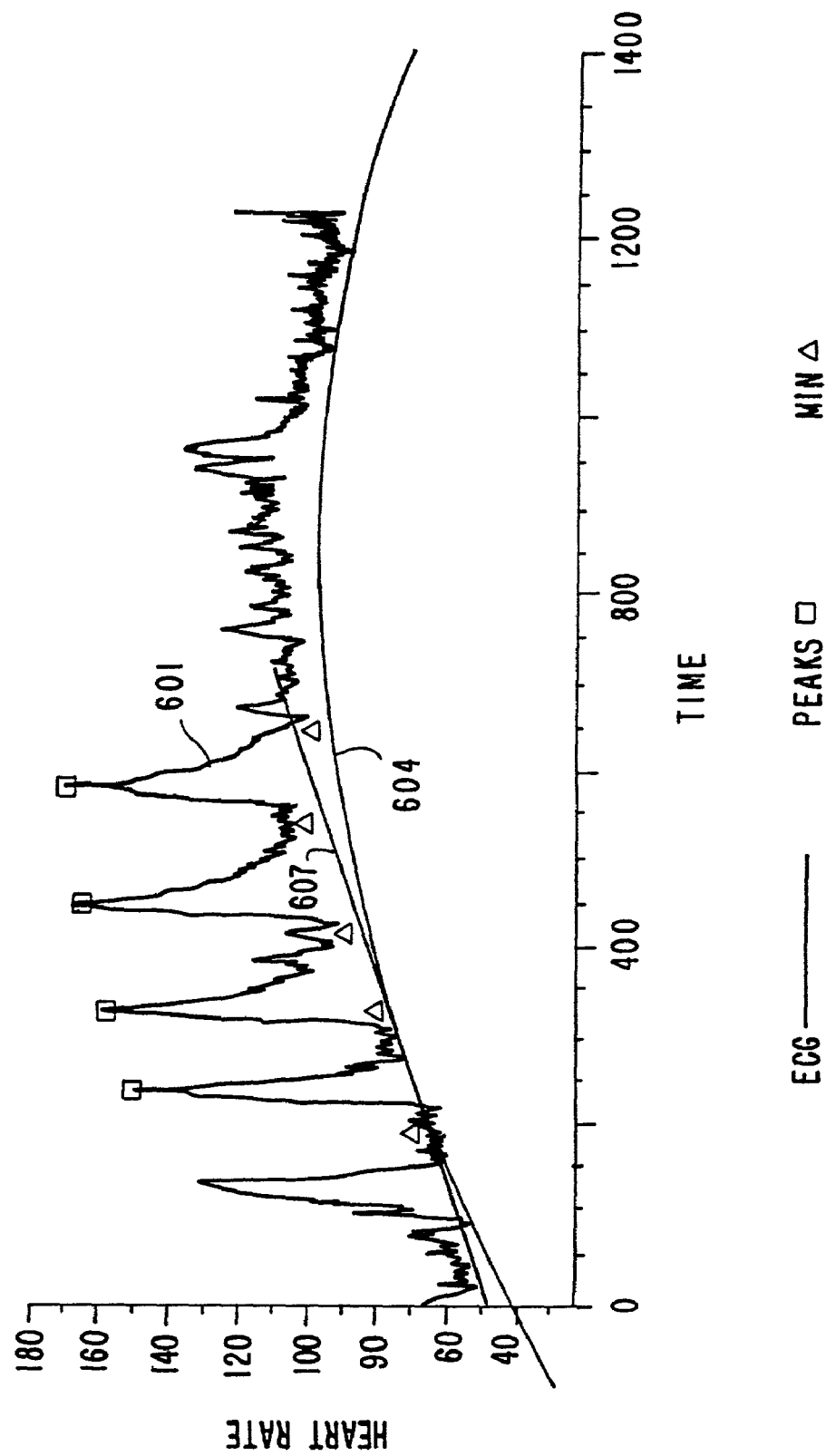
FIGS. 6a, 6b and 6c show three illustrative time traces having cumulative rest portions with varying degrees of parabolicity corresponding to good, moderate and poor physiological conditions, respectively.
Figure 6B:
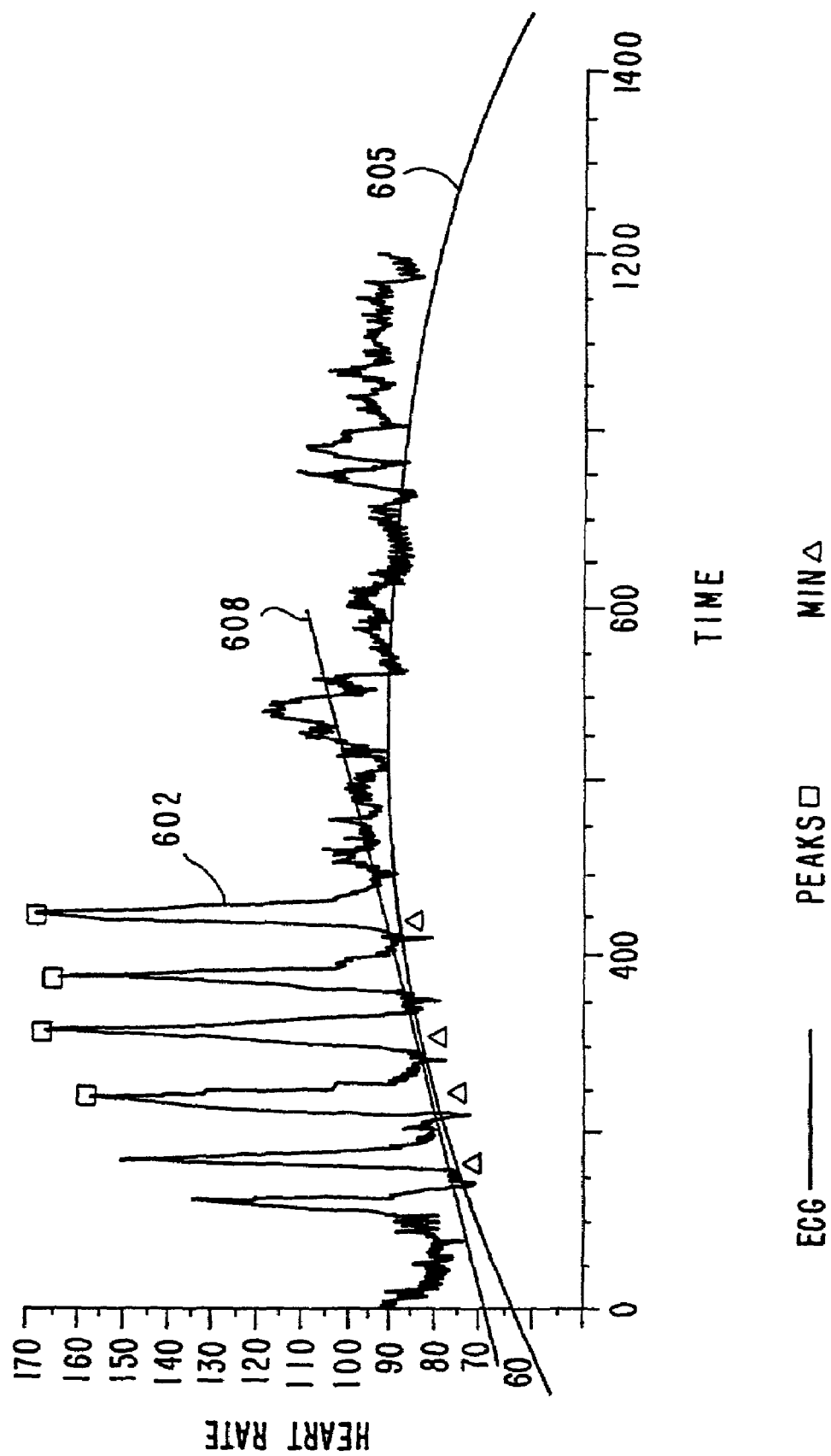
Figure 6C:
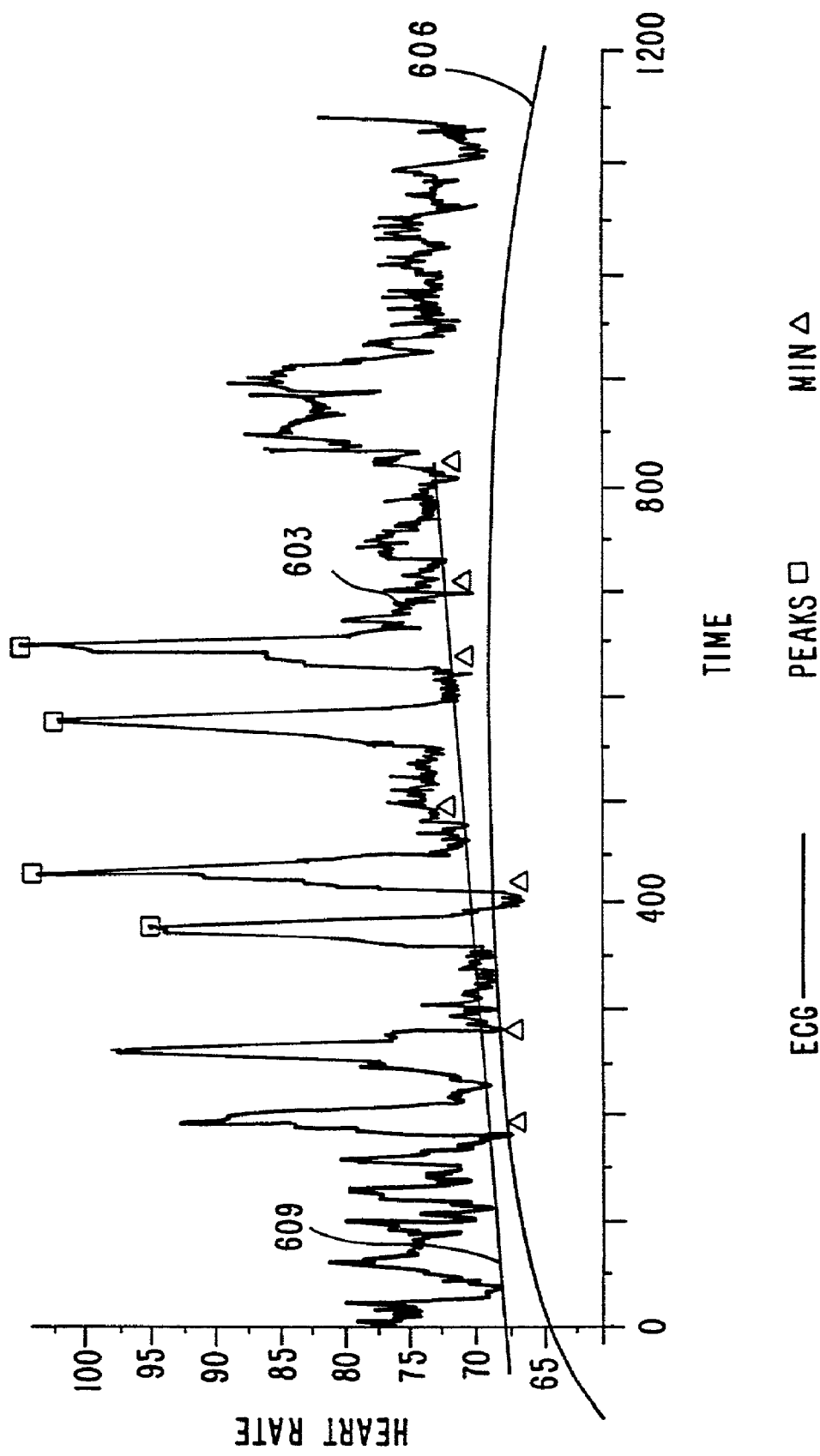

FIGS. 6a, 6b, and 6c show actual measured time traces 601, 602, and 603, of heart rate data from three different individuals. The time traces represent heart rate data collected over exercise sessions consisting of five exercise cycles (i.e., trace 601 and 602) or six exercise cycles (I e., trace 603). Analysis of pre-exercise rest portions of these traces yields baseline heart rates of 86, 58, and 78 beats per minute, respectively.

Analysis also includes identification of peak heart rates and minimum heart rates for each of the last four exercise cycles in each trace. The peak heart rates are indicated by square symbols in FIGS. 6a, 6b, and 6c. The peak heart rates for the last four cycles in trace 601, in descending order, are 169, 164, 158, and 149 beats per minute. Similarly, for trace 602 the peak heart rates are 169, 165, 168, and 158 beats per minute, and for trace 603 the peak heart rates are 105, 102, 104, and 95 beats per minute.

Analysis also includes calculating upward and downward slopes for the last exercise cycle in each trace. For traces 601, 602, and 603, upward and downward slope pairs have values of (48, 24), (72, 60) and (24, 24), respectively.

In each of FIGS. 6a, 6b, and 6c, the pre-exercise rest portion, the intervening rest portions, and the post-exercise rest portion can be combined to form a cumulative rest portion. Analysis of the leading edge of the cumulative rest portions yields baseline slopes that are positive. The magnitude of these slopes is proportional to the rate of increase of base line heart rates during the exercise sessions. The baseline slopes for traces 601, 602, and 603 are 150.9, 60.3, and 9.4, respectively. These baseline slopes are exemplified with lines 607, 608, and 609, respectively. It has been empirically found that the baseline slope correlates positively with an individual's physiological condition. It is believed that higher (i.e., steeper) baseline slopes correspond to better physiological conditions. Thus, measurement of a baseline slope can be used to assess an individual's physiological condition and to monitor an individual's progress.

Based on these peak and base line heart rates, baseline, upward, and downward slopes, heart wave indices for each individual are calculated, for example, according to:

$$\text{HWI} = (\text{peak heart rate of last cycle}) + \text{baseline slope}$$

By this analysis of traces 601, 602, and 603, heart wave indices of 320, 229, and 114 are obtained for the three different individuals, respectively. The relatively low heart wave index of 114 obtained from the analysis of trace 603 correlates positively with the poor physiological condition of the third individual, who was clinically found to suffer from congestive heart disease.

The shape cumulative rest portions of time traces 601, 602, and 603 exhibit different degrees of parabolicity, which are believed to correspond to good, moderate, and poor physiological conditions, respectively. As an alternate or in addition to baseline slopes, the degree of parabolicity can be quantified by fitting a parabola to the cumulative rest portion. Fitted parabolas 604–606 exhibiting varying degrees of parabolicity are shown in FIGS. 6a, 6b, and 6c, respectively.

Catalogs can be prepared that link measured coefficients and goodness of fit parameters, or other theoretical models (e.g., based on baseline slopes) to one or more specific abnormal physiological conditions. These catalogs can be based upon actual clinical data and/or theoretical data.

Abnormal physiological conditions then, can be diagnosed by fitting a parabola through one or more portions of the time trace (e.g., a top portion or a resting portion) to obtain parabolic coefficients and/or goodness of fit parameters. Abnormal physiological conditions can then be identified by determining which of the measured parabolic coefficients and/or goodness of fit parameters are like those listed in the catalog. Abnormal physiological conditions which may be amenable to diagnosis in this manner, can include conditions, such as congestive heart disease, leukemia, anorexia, multiple sclerosis, HIV or other immune deficiencies, astrocytoma of the brain, peripheral ischemia and neuropathy, ileitis, chronic hepatitis, and chronic fatigue syndrome.

The present invention also can be used to modify an exercise regimen. First, a representative heart wave index for an individual exercising under the regimen is obtained. This heart wave index may represent the results of analyzing time traces from one or more exercise sessions. For example, the representative heart wave index may represent the average of heart wave indices from the analysis of two consecutive exercise sessions, or the average of highest three of five exercise sessions.

The representative heart wave index is then compared to a target heart wave index associated with the exercise regimen. This comparison is used to determine a need to modify the exercise regimen, such as when the comparison indicates that the individual is not benefitting from the exercise regimen. The exercise regimen can be modified to make it more appropriate to the individual's physiological condition, for example, by raising the target heart rates. In one embodiment of the present invention, the target heart rate can be changed in direct proportion to the difference between the target heart wave index and the representative heart wave index. For example, if the representative heart wave index exceeds the target heart wave index by an amount (e.g., by 20 units), then the target heart rates in the previous regimen can be uniformly increased by one half of the difference (i.e., by 10 units) in the modified regimen.

An individual's initial physiological capability can be determined and used to individually tailor and prescribe an exercise regimen.

For example, an individual can be subject to an "exercise test" during which the individual's heart rate is monitored. A time trace is recorded, for example, on a chart recorder or any other electronic recording device.

The exercise test can include a plurality of test cycles that may be designed to be similar to the exercise cycle described above. The first few cycles can be warm-up cycles, followed by a plurality of intermediate cycles, which are then followed by at least one maximum effort cycle.

The warm-up cycles can or cannot have defined target heart rates. The intermediate cycles preferably have target heart rates. Most preferably, each of the intermediate cycles have a target heart rate that is greater than that of its immediately preceding cycle. The increase in target heart rates could vary substantially over an exercise session and in some cases decrease. The amount of the increase, however, is generally less than about 15 beats per minute. A maximum effort cycle does not have a fixed target heart rate but requires that the individual exercise up to the individual's maximum physical capability.

Test cycles can include a stress portion over a fixed time interval of between about 30 seconds and about 90 seconds, followed by a relaxation portion over another time interval. Preferably, the stress portion is over a time interval that is not in excess of about one minute. The relaxation portion need not be fixed and could be determined by the time it takes the individual's heart rate to recover and stabilize.

The individual's capability can be assessed in terms of a quantitative figure of merit based on cycle parameters obtained by analyzing the exercise cycles' time trace. In one embodiment, maximum heart rate $R_{max}$, which is achieved by the individual during each of the test cycles, is determined by analyzing the time trace as described above. Then, a capacity index is assigned a value that is a function of one or more maximum heart rates. For example, the capacity index can be assigned a value equal to the average of maximum heart rates achieved during two consecutive maximum effort cycles. Alternatively, a weighted sum could be used.

The time trace can be further analyzed to determine upward slopes and downward slopes in the manner discussed above. Then, the capacity index can be assigned a value based on one or more of test cycle parameters, such as maximum heart rates, upward slopes, and downward slopes. For example, the capacity index can be assigned a value equal to a straight or weighted sum or product of a maximum heart rate, upward slope, and downward slope of a maximum effort cycle.

Figure 7:
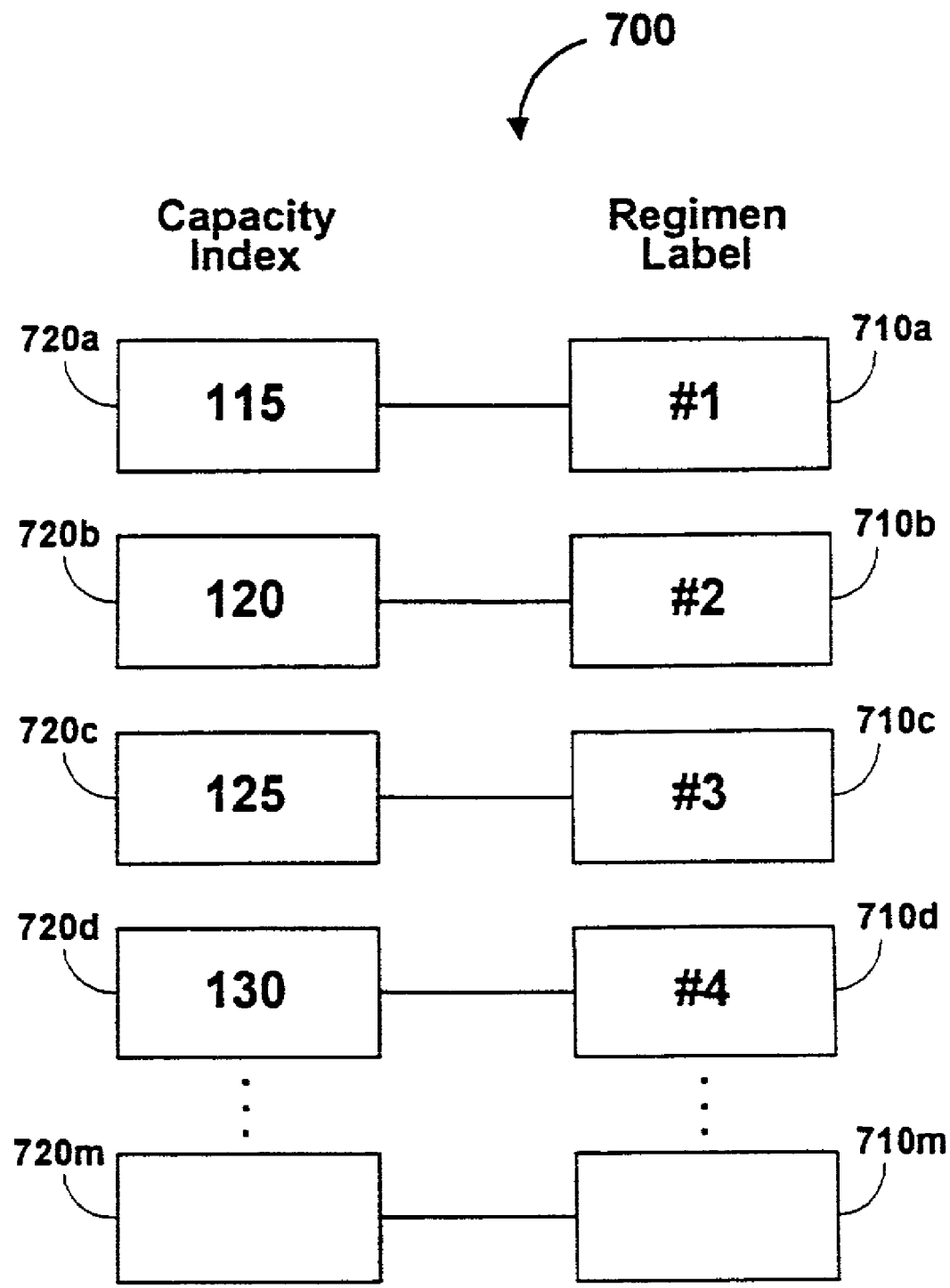
FIG. 7 is an illustrative look-up table that can be used in accordance with this invention.

Once a capacity index is determined, an exercise regimen can be generated. A heart wave index can also be used to generate the regimen. For example, a metric, such as the capacity index or heart wave index, can be received. Then, an individualized exercise regimen can be generated using an algorithm that relates the metric to the regimen. One or both of the receiving and generating steps can use a look-up table. FIG. 7 shows illustrative look-up table 700. Look-up table 700 includes a plurality of capacity indices 720*a*–720*m* and a plurality of predetermined exercise regimens 710*a*–710*m* that are respectively linked to the capacity indices. Capacity indices 720*a*–720*m* range from 115 to 180 in steps of five units but can have any range and any size steps.

The use of a look-up table can involve rounding the received metric to a nearest multiple of five or ten units, and then prescribing the exercise regimen corresponding to the rounded number. For example, a received index of 142 can be rounded to 140 (index 720*d*). Then, using look-up table 700, exercise regimen 710*d* can be selected and prescribed.

Exercise regimens 710*a*–710*m* can be empirically generated. In this case, the regimens preferably account for the wave nature of cardiac activity and apply the principles for therapeutic treatment and bio-rhythmic feed back taught by Dardik, U.S. Pat. Nos. 5,800,737, 5,752,521, 5,163,439, and 5,007,430, incorporated by reference herein. Appendix A, for example, contains an actual set of exercise regimens designed for individual's with capacity indices ranging from 115 to 180 units. The exercise regimens of Appendix A can be used, for example, in look-up table 700.

Each of regimens 710*a*–710*m* can include a plurality of exercise sessions to be performed by the individual over a time period. The time period can be any convenient period of time, such as about one lunar month. Each exercise session preferably includes a plurality of exercise cycles. The exercise cycles can include one or more warm-up cycles and one or more critical cycles that have target heart rates based on a metric.

The features of these exercise regimens can be better understood in conjunction with FIG. 8, which shows illustrative one month exercise regimen 800 starting Apr. 25, 2000. Regimen 800 is designed for individuals with capacity index 810 having a nominal value of about 115 units. Regimen 800 includes eleven exercise sessions 821–831 and rest week 832. Each of sessions 821–831 includes a plurality of exercise cycles, each of which is designated by a target heart rate and can contain a break if desired.

The time period over which the sessions are performed can begin with an initial rest period (not shown), end with a final rest period (rest week 832), and include intervening rest periods (April 26, April 28–29, May 1, May 3, May 5–6, May 8, May 10, May 12–13, May 15, and May 17) between the exercise sessions. Intervening rest periods are preferably at least about one day long, while final rest period 832 can be between about 4 days and about 10 days. Regimen 800 is to be performed over about four weeks (including final rest week 823).

The sessions in an exercise regimen can be synchronized with a lunar cycle. In FIG. 8, for example, regimen 800 is scheduled to start on Apr. 25, 2000 about three weeks prior to a full moon. The exercise sessions can also be synchronized with a circadian rhythm of the individual. For example, in FIG. 8 sessions 821–824, which are to be performed during the first week of the regimen, are scheduled between 6 a.m. and 9 a.m. This time period corresponds to a period of low circadian activity. Sessions 825–827, which are to be performed during the second week of the regimen, are scheduled to be performed between 9 a.m. and 12 p.m. This time period corresponds to a period of moderate circadian activity. Sessions 828–831, which are to be performed in the third week are scheduled to be performed between 3 p.m. and 6 p.m. This period corresponds to a period of high circadian activity.

The regimens used in the present invention can have a plurality of critical cycles that have sequentially increasing target heart rates. As used herein, a critical cycle is a cycle that has an associated target heart rate (i.e., is not a warm-up cycle without a defined target heart rate). For example, in session 821 the target heart rates increase sequentially for the first four cycles from 94 beats per minute to 114 beats per minute, and again increase sequentially for the last three cycles from 108 beats per minute to 118 beats per minute. It will be appreciated that the first set of four cycles has a lower initial target heart rate than the second set of three cycles.

Also, the initial target heart rate of the second set can be lower than the final target heart rate of the first set. Preferably, the target heart rates for critical cycles within an exercise session increase substantially superlinearly from one cycle to the next.

Critical cycles can have target heart rates that range up to about 20 beats above the metric being used. For example, sessions 830 and 831 have critical cycles with target heart rates of 130 beats per minute, which is 15 beats per minute higher than the nominal capacity index (i.e., 115).

Substantially all exercise sessions include a maximum cycle that has a target heart rate that is greater than that for its previous cycle. Preferably, the target heart rates for the maximum cycles increase substantially linearly from one session to the next. For example, in sessions 821–831, the highest target heart rate in each session sequentially increases in small increments from 118 beats per minute to 130 beats per minute (with the exception of a small decrease for session 823). Also, a regimen can include exercise cycles that alternate with rest periods.

One or more sessions in a regimen can include one or more spike cycles, during which the individual is expected to attempt to reach the target heart rate as rapidly as possible. In FIG. 8, for example, spike cycles are designated by the symbol "S" which is located next to the target heart rates.

The regimen can be divided into an earlier part and a later part, with the later part having more spike cycles than the early part. For example, in FIG. 8, sessions 821–825 are scheduled to be performed in the first week or so and include no spike cycles, while sessions 827–831 are scheduled to be performed in the second and third weeks and include several spike cycles.

Regimens provided by this invention can be accompanied by an instruction guide that includes instructions on how to perform the regimen. For example, an instruction could be included that directs the individual to abruptly stop exercising and to rest during a subsequent rest period. An instruction could also be included to exercise as vigorously as possible during a spike cycle.

The aforementioned methods can be implemented on systems that include an analyzer that preferably is programmable with routines that are capable of processing data contained in a time trace.

For example, the analyzer can include one or more routines for deriving one or more cycle parameters (such as a maximum heart rate, an upward slope, a downward slope, a peak heart rate, a resting heart rate, and a base line slope) from a time trace. The analyzer can also include routines that use regression analysis for fitting a parabola through a portion of the time trace, and routines for diagnosing abnormal physiological conditions by comparing measured parameters with those in a catalog that are linked with a physiological condition.

The analyzer can also include routines that compare a measured heart wave index to a target heart wave index and then modify an exercise regimen in response to the comparison.

In an yet another embodiment the analyzer can include a routine to receive a metric such as a heart wave index or a capacity index, a routine to generate an exercise regimen using an algorithm that relates the metric to the regimen, and a routine to provide the individual with the exercise regimen. The algorithm that relates the metric to the exercise regimen can use, for example, a previously prepared look-up table.

As used herein, electronic networks could include a local area network, a wireless network, a wired network, a wide area network, the Internet, and any combination thereof. An electronic network can provide links to user interfaces used for sending or receiving data. The interfaces can be any one or more of commercially available interface devices such as a web page, a web browser, a plug-in, a display monitor, a computer terminal, a modem, an audio device, a tactile device (e.g., vibrating surface, etc.), or any combination thereof.

In accordance with the present invention, software (i.e., instructions) for controlling the aforementioned systems can be provided on computer-readable media. It will be appreciated that each of the steps (described above in accordance with this invention), and any combination of these steps, can be implemented by computer program instructions. These computer program instructions can be loaded onto a computer or other programmable apparatus to produce a machine, such that the instructions which execute on the computer or other programmable apparatus create means for implementing the functions specified in the flowchart block or blocks. These computer program instructions can also be stored in a computer-readable memory that can direct a computer or other programmable apparatus to function in a particular manner, such that the instructions stored in the computer-readable memory produce an article of manufacture including instruction means which implement the function specified in the flowchart block or blocks. The computer program instructions can also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the flowchart block or blocks.

It will be understood that the foregoing is only illustrative of the principles of the invention, and that various modifications can be made by those skilled in the art without departing from the scope and spirit of the invention.

Appendix A

| REGIMEN beginning Apr. 25 | | | |
|---|---|---|---|
| CAPACITY INDEX: 115'S | | | |
| 6–9 AM | 6–9 AM | 6–9 AM | 6–9 AM |
| Tue Apr. 25 | Thu Apr. 27 | Sun Apr. 30 | Tue May 2 |
| 94 | 98 | 100 | 102 |
| 103 | 109 | 107 | 109 |
| 111 | 114 | 112 | 116 |
| 114 | 5 min. break | 115 | 117 |
| 10 min. break | 111 | 119 | 122 |
| 108 | 117 | | |
| 115 | 120 | | |
| 118 | | | |
| 9–12 AM | 9–12 AM | 9–12 AM | |
| Thu May 4 | Sun May 7 | Tue May 9 | |
| 104 | 108 | 111 | |
| 114 | 116 | 118 (S) | |
| 118 (S) | 122 (S) | 124 (S) | |
| 122 | | | |
| 3–6 PM | 3–6 PM | 3–6 PM | 3–6 PM |
| ThuMay11 | Sun May 14 | Tue May 16 | Thu May 18 |

-continued

REGIMEN
beginning Apr. 25

| 106 | 110 | 113 | 115 |
|---|---|---|---|
| 115 | 118 (S) | 118 (S) | 121 (S) |
| 119 | 121 (S) | 121 (S) | 130 (S) |
| 123 (S) | 124 (S) | 122 (S) | |
| 120 (S) | | 130 (S) | |
| 124 | | | |

CAPACITY INDEX: 120'S

| 6–9 AM Tue Apr. 25 | 6–9 AM Thu Apr. 27 | 6–9 AM Sun Apr. 30 | 6–9 AM Tue May 2 |
|---|---|---|---|
| 96 | 100 | 102 | 104 |
| 102 | 112 | 110 | 112 |
| 114 | 117 | 116 | 120 |
| 118 | 5 min. break | 119 | 121 |
| 10 min. break | 114 | 123 | 126 |
| 111 | 121 | | |
| 119 | 124 | | |
| 122 | | | |

| 9–12 AM Thu May 4 | 9–12 AM Sun May 7 | 9–12 AM Tue May 9 | |
|---|---|---|---|
| 106 | 110 | 113 | |
| 118 | 120 | 122 (S) | |
| 123 (S) | 127 (S) | 129 (S) | |
| 127 | | | |

| 3–6 PM ThuMay11 | 3–6 PM Sun May 14 | 3–6 PM Tue May 16 | 3–6 PM Thu May 18 |
|---|---|---|---|
| 108 | 112 | 115 | 117 |
| 119 | 122 (S) | 121 (S) | 125 (S) |
| 123 | 126 (S) | 125 (S) | 135 (S) |
| 128 (S) | 129 (S) | 127 (S) | |
| 125 (S) | | 135 (S) | |
| 129 | | | |

CAPACITY INDEX: 125'S

| 6–9 AM Tue Apr. 25 | 6–9 AM Thu Apr. 27 | 6–9 AM Sun Apr. 30 | 6–9 AM Tue May 2 |
|---|---|---|---|
| 98 | 102 | 104 | 106 |
| 105 | 115 | 114 | 115 |
| 118 | 121 | 120 | 124 |
| 122 | 5 min. break | 124 | 125 |
| 10 min. break | 118 | 128 | 131 |
| 114 | 125 | | |
| 123 | 129 | | |
| 127 | | | |

| 9–12 AM Thu May 4 | 9–12 AM Sun May 7 | 9–12 AM Tue May 9 | |
|---|---|---|---|
| 118 | 112 | 115 | |
| 121 | 123 | 126 (S) | |
| 127 (S) | 132 (S) | 134 (S) | |
| 132 | | | |

| 3–6 PM ThuMay11 | 3–6 PM Sun May 14 | 3–6 PM Tue May 16 | 3–6 PM Thu May 18 |
|---|---|---|---|
| 110 | 114 | 117 | 119 |
| 122 | 125 (S) | 124 (S) | 129 (S) |
| 127 | 130 (S) (BD) | 129 (S) | 140 (S) |
| 133 (S) | 134 (S) | 131 (S) | |
| 129 (S) | | 140 (S) | |
| 134 | | | |

-continued

REGIMEN
beginning Apr. 25

CAPACITY INDEX: 130'S

| 6–9 AM Tue Apr. 25 | 6–9 AM Thu Apr. 27 | 6–9 AM Sun Apr. 30 | 6–9 AM Tue May 2 |
|---|---|---|---|
| 100 | 104 | 106 | 108 |
| 107 | 118 | 117 | 118 |
| 121 | 124 | 124 | 128 |
| 126 | 5 min. break | 128 | 129 |
| 10 min. break | 121 | 132 | 135 |
| 117 | 129 | | |
| 127 | 133 | | |
| 131 | | | |

| 9–12 AM Thu May 4 | 9–12 AM Sun May 7 | 9–12 AM Tue May 9 | |
|---|---|---|---|
| 110 | 114 | 117 | |
| 125 | 127 | 130 (S) | |
| 132 (S) | 137 (S) | 139 (S) | |
| 137 | | | |

| 3–6 PM Thu May 11 | 3–6 PM Sun May 14 | 3–6 PM Tue May 16 | 3–6 PM Thu May 18 |
|---|---|---|---|
| 112 | 116 | 119 | 121 |
| 126 | 129 (S) | 127 (S) | 133 (S) |
| 131 | 135 (S) | 133 (S) | 145 (S) |
| 138 (S) | 139 (S) | 136 (S) | |
| 134 (S) | | 145 (S) | |
| 139 | | | |

CAPACITY INDEX: 135'S

| 6–9 AM Tue Apr. 25 | 6–9 AM Thu Apr. 27 | 6–9 AM Sun Apr. 30 | 6–9 AM Tue May 2 |
|---|---|---|---|
| 102 | 106 | 108 | 110 |
| 110 | 121 | 121 | 121 |
| 125 | 128 | 128 | 132 |
| 130 | 5 min brk | 133 | 133 |
| 10 min brk | 125 | 137 | 140 |
| 120 | 133 | 131 | 138 |
| 136 | | | |

| 9–12 AM Thu May 4 | 9–12 AM Sun May 7 | 9–12 AM Tue May 9 | |
|---|---|---|---|
| 112 | 116 | 119 | |
| 128 | 130 | 134 (S) | |
| 136 (S) | 142 (S) | 144 (S) | |
| 142 | | | |

| 3–6 PM Thu May 11 | 3–6 PM Sun May 14 | 3–6 PM Tue May 16 | 3–6 PM Thu May 18 |
|---|---|---|---|
| 114 | 118 | 121 | 123 |
| 114 | 118 (S) | 121 (S) | 123 (S) |
| 135 | 139 (S) | 137 (S) | 150 (S) |
| 143 (S) | 144 (S) | 140 (S) | |
| 138 (S) | 150 (S) | | |
| 144 | | | |

CAPACITY INDEX: 140'S

| 6–9 AM Tue Apr. 25 | 6–9 AM Thu Apr. 27 | 6–9 AM Sun Apr. 30 | 6–9 AM Tue May 2 |
|---|---|---|---|
| 104 | 108 | 110 | 112 |
| 112 | 124 | 123 | 124 |
| 128 | 132 | 132 | 136 |
| 134 | 5 min. break | 136 | 137 |
| 10 min. break | 128 | 141 | 144 |
| 124 | 137 | | |

-continued

REGIMEN
beginning Apr. 25

| 135 | 142 |
| --- | --- |
| 140 | |

| 9–12 AM<br>Thu May 4 | 9–12 AM<br>Sun May 7 | 9–12 AM<br>Tue May 9 |
| --- | --- | --- |
| 114 | 118 | 121 |
| 132 | 134 | 138 (S) |
| 141 (S) | 147 (S) | 149 (S) |
| 147 | | |

| 3–6 PM<br>Thu May 11 | 3–6 PM<br>Sun May 14 | 3–6 PM<br>Tue May 16 | 3–6 PM<br>Thu May 18 |
| --- | --- | --- | --- |
| 116 | 120 | 123 | 125 |
| 133 | 136 (S) | 133 (S) | 141 (S) |
| 139 | 144 (S) | 141 (S) | 155 (S) |
| 148 (S) | 149 (S) | 145 (S) | |
| 141 (S) | | 155 (S) | |
| 149 | | | |

CAPACITY INDEX: 145'S

| 6–9 AM<br>Tue Apr. 25 | 6–9 AM<br>Thu Apr. 27 | 6–9 AM<br>Sun Apr. 30 | 6–9 AM<br>Tue May 2 |
| --- | --- | --- | --- |
| 106 | 110 | 112 | 114 |
| 115 | 128 | 127 | 128 |
| 132 | 137 | 137 | 141 |
| 139 | 5 min. break | 141 | 142 |
| 10 min. break | 132 | 146 | 149 |
| 128 | 142 | | |
| 139 | 147 | | |
| 145 | | | |

| 9–12 AM<br>Thu May 4 | 9–12 AM<br>Sun May 7 | 9–12 AM<br>Tue May 9 |
| --- | --- | --- |
| 116 | 120 | 123 |
| 135 | 138 | 142 (S) |
| 145 (S) | 152 (S) | 154 (S) |
| 152 | | |

| 3–6 PM<br>Thu May 11 | 3–6 PM<br>Sun May 14 | 3–6 PM<br>Tue May 16 | 3–6 PM<br>Thu May 18 |
| --- | --- | --- | --- |
| 118 | 122 | 125 | 127 |
| 137 | 140 (S) | 136 (S) | 145 (S) |
| 143 | 148 (S) | 145 (S) | 160 (S) |
| 153 (S) | 154 (S) | 149 (S) | |
| 145 (S) | | 160 (S) | |
| 154 | | | |

CAPACITY INDEX: 150'S

| 6–9 AM<br>Tue Apr 25 | 6–9 AM<br>Thu Apr. 27 | 6–9 AM<br>Sun Apr. 30 | 6–9 AM<br>Tue May 2 |
| --- | --- | --- | --- |
| 108 | 112 | 114 | 116 |
| 117 | 130 | 129 | 130 |
| 135 | 140 | 140 | 144 |
| 142 | 5 min. break | 144 | 145 |
| 10 min. break | 135 | 150 | 153 |
| 131 | 145 | | |
| 143 | 151 | | |
| 149 | | | |

| 9–12 AM<br>Thu May 4 | 9–12 AM<br>Sun May 7 | 9–12 AM<br>Tue May 9 |
| --- | --- | --- |
| 118 | 122 | 125 |
| 139 | 141 | 146 (S) |
| 150 (S) | 157 (S) | 159 (S) |
| 157 | | |

| 3–6 PM<br>Thu May 11 | 3–6 PM<br>Sun May 14 | 3–6 PM<br>Tue May 16 | 3–6 PM<br>Thu May 18 |
| --- | --- | --- | --- |
| 120 | 124 | 127 | 129 |
| 140 | 143 (S) | 139 (S) | 149 (S) |
| 147 | 153 (S) | 149 (S) | 165 (S) |
| 158 (S) | 159 (S) | 154 (S) | |
| 150 (S) | | 165 (S) | |
| 159 | | | |

CAPACITY INDEX: 160'S

| 6–9 AM<br>Tue Apr. 25 | 6–9 AM<br>Thu Apr. 27 | 6–9 AM<br>Sun Apr. 30 | 6–9 AM<br>Tue May 2 |
| --- | --- | --- | --- |
| 112 | 116 | 118 | 120 |
| 122 | 136 | 135 | 136 |
| 142 | 148 | 148 | 152 |
| 150 | 5 min. break | 152 | 153 |
| 10 min. break | 142 | 159 | 162 |
| 138 | 153 | | |
| 151 | 160 | | |
| 158 | | | |

| 9–12 AM<br>Thu May 4 | 9–12 AM<br>Sun May 7 | 9–12 AM<br>Tue May 9 |
| --- | --- | --- |
| 122 | 126 | 129 |
| 146 | 148 | 154 (S) |
| 159 (S) | 167 (S) | 169 (S) |
| 167 | | |

| 3–6 PM<br>Thu May 11 | 3–6 PM<br>Sun May 14 | 3–6 PM<br>Tue May 16 | 3–6 PM<br>Thu May 18 |
| --- | --- | --- | --- |
| 124 | 128 | 131 | 133 |
| 147 | 150 (S) | 145 (S) | 157 (S) |
| 155 | 162 (S) | 157 (S) | 175 (S) |
| 168 (S) | 169 (S) | 163 (S) | |
| 159 (S) | | 175 (S) | |
| 169 | | | |

CAPACITY INDEX: 170'S

| 6–9 AM<br>Tue Apr. 25 | 6–9 AM<br>Thu Apr. 27 | 6–9 AM<br>Sun Apr. 30 | 6–9 AM<br>Tue May 2 |
| --- | --- | --- | --- |
| 116 | 120 | 122 | 124 |
| 125 | 142 | 141 | 142 |
| 149 | 156 | 156 | 160 |
| 158 | 5 min break | 160 | 161 |
| 10 min. break | 149 | 168 | 171 |
| 145 | 161 | | |
| 159 | 169 | | |
| 167 | | | |

| 9–12 AM<br>Thu May 4 | 9–12 AM<br>Sun May 7 | 9–12 AM<br>Tue May 9 |
| --- | --- | --- |
| 126 | 130 | 133 |
| 153 | 155 | 162 (S) |
| 168 (S) | 177 (S) | 179 (S) |
| 177 | | |

| 3–6 PM<br>Thu May 11 | 3–6 PM<br>Sun May 14 | 3–6 PM<br>Tue May 16 | 3–6 PM<br>Thu May 18 |
| --- | --- | --- | --- |
| 128 | 132 | 135 | 137 |
| 154 | 157 (S) | 151 (S) | 165 (S) |
| 163 | 171 (S) | 165 (S) | 185 (S) |
| 178 (S) | 179 (S) | 172 (S) | |
| 168 (S) | | 185 (S) | |
| 179 | | | |

-continued

REGIMEN
beginning Apr. 25

CAPACITY INDEX: 175'S

| 6–9 AM<br>Tue Apr. 25 | 6–9 AM<br>Thu Apr. 27 | 6–9 AM<br>Sun Apr. 30 | 6–9 AM<br>Tue May 2 |
|---|---|---|---|
| 118 | 122 | 124 | 126 |
| 130 | 145 | 145 | 145 |
| 153 | 160 | 160 | 164 |
| 162 | 5 min. break | 165 | 165 |
| 10 min. break | 153 | 173 | 176 |
| 148 | 165 | | |
| 163 | 174 | | |
| 172 | | | |

| 9–12 AM<br>Thu May 4 | 9–12 AM<br>Sun May 7 | 9–12 AM<br>Tue May 9 |
|---|---|---|
| 128 | 132 | 135 |
| 156 | 158 | 166 (S) |
| 172 (S) | 182 (S) | 184 (S) |
| 182 | | |

| 3–6 PM<br>Thu May 11 | 3–6 PM<br>Sun May 14 | 3–6 PM<br>Tue May 16 | 3–6 PM<br>Thu May 18 |
|---|---|---|---|
| 130 | 134 | 137 | 139 |
| 157 | 160 (S) | 154 (S) | 169 (S) |
| 167 | 175 (S) | 169 (S) | 190 (S) |
| 183 (S) | 184 (S) | 176 (S) | |
| 172 (S) | | 190 (S) | |
| 184 | | | |

CAPACITY INDEX: 180'S

| 6–9 AM<br>Tue Apr. 25 | 6–9 AM<br>Thu Apr. 27 | 6–9 AM<br>Sun Apr. 30 | 6–9 AM<br>Tue May 2 |
|---|---|---|---|
| 120 | 124 | 126 | 128 |
| 132 | 148 | 147 | 148 |
| 156 | 164 | 164 | 168 |
| 166 | 5 min break | 168 | 169 |
| 10 min break | 156 | 177 | 180 |
| 152 | 169 | | |
| 167 | 178 | | |
| 176 | | | |

| 9–12 AM<br>Thu May 4 | 9–12 AM<br>Sun May 7 | 9–12 AM<br>Tue May 9 |
|---|---|---|
| 130 | 134 | 137 |
| 160 | 162 | 170 (S) |
| 177 (S) | 187 (S) | 189 (S) |
| 187 | | |

| 3–6 PM<br>Thu May 11 | 3–6 PM<br>Sun May 14 | 3–6 PM<br>Tue May 16 | 3–6 PM<br>Thu May 18 |
|---|---|---|---|
| 132 | 136 | 139 | 141 |
| 161 | 164 (S) | 157 (S) | 173 (S) |
| 171 | 180 (S) | 173 (S) | 195 (S) |
| 188 (S) | 189 (S) | 181 (S) | |
| 177 (S) | | 195 (S) | |
| 189 | | | |

We claim:

1. A computer-readable medium containing instructions for prescribing an exercise regimen for an individual, said instructions comprising:
    instructions to receive a metric indicative of said individual's physiological condition;
    instructions to generate said exercise regimen using an algorithm that relates said metric to said regimen;
    instructions to export said exercise regimen to said individual using an output device; and
    instructions for generating a guide based on said regimen, said guide directing said individual in real-time on how to exercise, wherein said metric is based on heart rate information of an individual obtained during an exercise test.

2. The computer-readable medium of claim 1 wherein said exercise regimen comprises a plurality of exercise sessions to be performed by said individual, wherein each of said plurality of exercise sessions comprising:
    at least one warm up cycle; and
    at least one critical cycle that has a target heart rate, wherein said target heart rate is based on said metric.

3. The computer-readable medium of claim 1 further comprising instructions to determine a capacity index based on an electronic file containing a time trace of a heart rate of said individual obtained during said exercise test that includes a plurality of test cycles and at least one maximum effort cycle, wherein said instructions to determine a capacity index comprises:
    instructions to determine at least one maximum effort cycle parameter; and
    instructions to determine said capacity index based on said at least one maximum effort cycle parameter.

4. The computer-readable medium of claim 3, wherein said maximum effort cycle parameter is selected from a group consisting of a first peak heart rate corresponding to a maximum heart rate monitored during said maximum effort cycle.

5. The computer-readable medium of claim 3, wherein said instructions to determine a capacity index further comprises instructions to determine another parameter for use in said capacity index, said another parameter being selected from a group consisting of a second peak heart rate monitored during another of said plurality of test cycles that is not said maximum effort cycle, an upward slope of said heart rate monitored during a part of a stress portion of at least one of said plurality of test cycles, and a downward slope of said heart rate monitored during a part of a relaxation portion of the at least one of said plurality of test cycles.

6. A computer-readable medium containing instructions for prescribing an exercise regimen for an individual, said instructions comprising:
    instructions to receive a metric indicative of said individual's physiological condition;
    instructions to generate said exercise regimen using an algorithm that relates said metric to said regimen;
    instructions to export said exercise regimen to said individual using an output device;
    instructions for generating a guide based on said regimen, said guide directing said individual in real-time on how to exercise; and
    instructions for communication over links within a system wherein said links comprise an electronic network selected from a group consisting of local area networks, wireless networks, wired networks, wide area networks, the Internet and any combination thereof.

7. A computer-readable medium containing instructions for prescribing an exercise regimen for an individual, said instructions comprising:
    instructions to receive a metric indicative of said individual's physiological condition;
    instructions to generate said exercise regimen using an algorithm that relates said metric to said regimen;
    instructions to export said exercise regimen to said individual using an output device;

instructions for generating a guide based on said regimen, said guide directing said individual in real-time on how to exercise; and instructions for accessing linked databases including said guide, through an electronic network, wherein said network is selected from a group comprising of a local area network, a wide area network, a wired network, a wireless network, the Internet and any combination thereof.

8. A computer-readable medium containing instructions for prescribing an exercise regimen for an individual, said instructions comprising:

instructions to receive a metric indicative of said individual's physiological condition;

instructions to generate said exercise regimen using an algorithm that relates said metric to said regimen;

instructions to export said exercise regimen to said individual using an output device;

instructions for generating a guide based on said regimen, said guide directing said individual in real-time on how to exercise; and instructions for controlling a system through an electronic network, wherein said network is selected from a group comprising of a local area network, a wide area network, a wired network, a wireless network, the Internet and any combination thereof.

9. A computer-readable medium containing instructions for prescribing an exercise regimen for an individual, said instructions comprising:

instructions to receive a metric indicative of said individual's physiological condition;

instructions to generate said exercise regimen using an algorithm that relates said metric to said regimen;

instructions to export said exercise regimen to said individual using an output device;

instructions for generating a guide based on said regimen, said guide directing said individual in real-time on how to exercise; and instructions for communication external to a system through user interfaces selected from a group comprising of web pages, display monitors, terminals, modems, audio devices, wired devices, and wireless devices or any combination thereof.

* * * * *